US007439416B2

(12) United States Patent
Evans

(10) Patent No.: US 7,439,416 B2
(45) Date of Patent: Oct. 21, 2008

(54) **INDETERMINATE GAMETOPHYTE 1 (*IG1*)GENE FROM *ZEA MAYS* AND USES THEREOF**

(75) Inventor: Matthew Evans, Stanford, CA (US)

(73) Assignee: The Carnegie Institution of Washington, Washington, DC (US)

( * ) Notice: Subject to any disclaimer, the term of this patent is extended or adjusted under 35 U.S.C. 154(b) by 0 days.

(21) Appl. No.: 11/030,329

(22) Filed: Jan. 7, 2005

(65) Prior Publication Data

US 2005/0198711 A1 Sep. 8, 2005

Related U.S. Application Data

(60) Provisional application No. 60/534,967, filed on Jan. 9, 2004.

(51) Int. Cl.
*C12N 15/82* (2006.01)
*A01H 5/00* (2006.01)
*C07H 21/04* (2006.01)

(52) U.S. Cl. .................. 800/286; 800/285; 800/290; 800/320.1; 435/320.1; 435/468; 435/419; 536/24.5; 536/23.1

(58) Field of Classification Search .................. None
See application file for complete search history.

(56) References Cited

U.S. PATENT DOCUMENTS 5,702,933 A * 12/1997 Klee et al. .................. 800/283
6,563,020 B1 * 5/2003 Simmons et al. ............ 800/279
2004/0216190 A1 * 10/2004 Kovalic ...................... 800/289

FOREIGN PATENT DOCUMENTS

WO WO 96/39803 * 12/1996

OTHER PUBLICATIONS

Kermicle J. L. Indeterminate Gametophyte (ig): Bioogy and Use. (1994) in The Maize Handbook—Freeling and Walbot, editors, Springer-Verlag, New York, pp. 388-393.*
Elomaa P. Transformation of antisense constructs of the chalcone synthase gene superfamily into Gerbera hybrida: differential effect on the expression of family members. (1996) Molecular Breeding, vol. 2, pp. 41-50.*
Colliver S. P. Differential modification of flavonoid and isoflavonoid biosynthesis with an antisense chalcone synthase construct in transgenic Lotus corniculatus. (1997) PMB, vol. 35, pp. 509-522.*
Lewin B. Genes V. (1994) Oxford University Press, pp. 882-883 and 889.*
Lacombe B. et al. The Identity of Plant Glutamate Receptors. (2001) Science, vol. 292, pp. 1486-1487.*
Whitelaw et al. Consortium for Maize Genomics. (2003) GenBank Accession CC634174, pp. 1-2.*
Addgene, Stratagene map of pBlueScript SK-, pp. 1-3.*

* cited by examiner

*Primary Examiner*—Medina A. Ibrahim
*Assistant Examiner*—Cathy Kingdon Worley
(74) *Attorney, Agent, or Firm*—Morgan, Lewis & Bockius LLP

(57) ABSTRACT

This invention provides the genes for indeterminate gametophyte (ig1), mutants of ig1, homologs of ig1, and orthologs of ig1, as well as the proteins encoded by these genes. This invention also provides compositions and methods which utilize these genes and proteins. Such methods include the creation of transgenic plants with antisense or expression constructs which comprise a nucleotide sequence derived from ig1.

14 Claims, 11 Drawing Sheets

INDETERMINATE GAMETOPHYTE 1 (*IG1*)GENE FROM *ZEA MAYS* AND USES THEREOF

RELATED APPLICATIONS

This application claims priority to U.S. provisional patent application Ser. No. 60/534,967 filed Jan. 9, 2004, which is herein incorporated by reference in its entirety.

STATEMENT OF RIGHTS TO INVENTIONS MADE UNDER FEDERALLY SPONSORED RESEARCH

This invention was partially made with government support under United States National Science Foundation Grant No. IBN-0296074, entitled "Genetic Control of Polar Nuclei Number in Maize." The U.S. government has certain rights in this invention.

FIELD OF THE INVENTION

This invention relates generally to the genetic control of polar nuclei number in plants. More specifically, this invention relates to the indeterminate gametophyte1 (ig1) gene cloned from *Zea mays*, mutations of the ig gene, and orthologs of the ig1 gene isolated from other plant species. The invention also relates to constructs and vectors comprising said genes, recombinant prokaryotic and eukaryotic cells comprising said genes and the use of said constructs and vectors to create transgenic plant cells, plant tissues and whole plants. In addition, this invention also relates to methods of using the genes to produce male sterility for plant breeding and for generating androgenetic progeny in maize (i.e., corn, *Zea mays*) and other plants species.

BACKGROUND OF THE INVENTION

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Plants have two phases to their life cycle: the diploid phase, or sporophyte, that ends in meiosis to produce haploid cells, and the haploid phase, or gametophyte, in which mitotic proliferation to produce a haploid plant includes differentiation of a subset of cells as gametes prepared for fertilization to reconstitute a diploid organism. Both the egg-producing haploid plant, the megagametophyte, and the sperm-producing haploid plant, the microgametophyte, are genetically active, hence gametophyte phenotype reflects haploid allele type. In contrast, gamete properties in animals are determined almost entirely by gene expression in progenitor diploid cells. Flowering plants are further distinguished from animals by the process of double fertilization. Two cells of the female gametophyte, the egg and central cell, are fertilized by two typically genetically identical sperm cells of the male gametophyte to produce the embryo and endosperm, respectively, of the seed.

In angiosperms the polygonum type of megasporogenesis is most common, occurring in 70% of species, including *Arabidopsis* and maize. In these plants the chalazal megaspore, one of the meiotic products of the megaspore mother cell, undergoes three rounds of free nuclear division followed by cellularization to give rise to a seven-celled embryo sac (FIG. 1). The free nuclear divisions are invariant in number, tightly regulated as indicated by their synchrony, and accompanied by stereotypical nuclear migrations. The angiosperm female gametophyte, called the embryo sac, consists of four cell types: synergids, antipodals, egg, and central cell (Drews et al., 1998; Grossniklaus and Schneitz, 1998; Yang and Sundaresan, 2000).

Despite the limited size of the gametophytes in flowering plants a very large number of genes are essential for haploid development. The gametophytes undergo mitosis, cell growth, and organelle biogenesis. Cells exchange signals for differentiation and for interaction with the surrounding diploid tissues. Gametophytes acquire attributes important in self vs. non-self recognition during pollination, and gametes acquire factors required for successful fertilization. Many basic cellular processes are required in gametophytes (e.g. tip growth of cells in the pollen tube of the microgametophyte; gamete fusion; cell-cell attraction; mitosis; cytokinesis; intracellular trafficking; cell death).

Demonstration that the entire genome, rather than specific chromosomes or a few chromosomal segments, are important comes from classical cytogenetic analyses in maize. In the ~3000 cM maize genetic map, there are only a few regions in which short deletions still permit production of viable gametes, i.e. 2 cM deletions from anther ear1 to bronze2 on chromosome 1 and from shrunken1 to bronze1 on chromosome 9 (Patterson, E. B. 1978). More convincingly Patterson and others exploited more than 850 reciprocal translocation stocks, representing 1700 deficiencies, to establish that all caused pollen abortion and about 90% resulted in megagametophyte lethality (Coe et al., 1988). Presumably some nutritional defects lethal to pollen, which is sealed from metabolic exchange with the surrounding diploid tissues for days, can be compensated for in megagametophytes, which continue to absorb nutrients from their diploid mother.

Gametophyte mutations result in characteristic phenotypes and modes of transmission. Heterozygotes for female gametophyte mutations are expected to have reduced fertility, because half of the embryo sacs inherit the mutant allele. Male gametophyte mutations do not cause reduced seed set because there is normally excess pollen. However, for both male and female gametophyte mutations the mutant allele is found at a reduced frequency in progeny when the affected gamete is involved in the cross. Because these mutations act after meiosis they are transmitted poorly or not at all, as are loci linked to them.

Mutations that act in the gametophyte generation have been identified recently in several species by screening for poor transmission through the gametes and for semisterility of mutant heterozygotes (Feldmann et al., 1997; Moore et al., 1997; Howden et al., 1998; Christensen et al., 1998; Christensen et al., 2002; Shimizu and Okada, 2000). The mutants fall into several categories: gametophytes that arrest early in development; well developed, but morphologically aberrant gametophytes and morphologically normal gametophytes that nevertheless fail to function. All developmental steps depicted in FIG. 1 are represented by at least one mutant. The largest class of mutants contains those that arrest development early. Although some of these mutations may be in genes with specific roles during embryo sac development, many of them likely are required for functions in all cell types. One example of this is *PROLIFERA of Arabidopsis* (Springer et al., 1995). PRO shows homology to MCM2-3-5 genes required for DNA replication and cell cycle control. The mutant phenotype, sequence, and expression pattern of PRO suggest it is required in all dividing cells.

SUMMARY OF THE INVENTION

The instant invention involves the maize indeterminate gametophyte1 (ig1) gene and the protein product of the gene. The instant invention provides a partial nucleic acid sequence for the maize indeterminate gametophyte1 (ig1) gene (SEQ ID NO: 1) and the corresponding protein product of the partial gene (SEQ ID NO: 2). The instant invention is further directed to mutations of the indeterminate gametophyte1 (ig1) gene, such as ig1-O and ig1-mum, and the protein products of those genes. The instant invention is further directed to orthologs of the indeterminate gametophyte1 (ig1) gene, wherein such orthologs are identified and cloned in other plant species, such as rice, by using the ig1 gene and mutations of the ig1 gene isolated from maize.

One object of the present invention is to provide maize ig1 nucleic acids and the IG1 protein produced thereby. The present invention also provides ig1 nucleic acids of *Zea mays* and the IG1 proteins they produce. The invention includes isolated nucleic acid molecules selected from the group consisting of isolated nucleic acid molecules that encode an amino acid sequence of IG1, IG1-O, IG1-MUM and orthologs of IG1. The present invention provides an isolated nucleic acid molecule that encodes a fragment of at least 6 amino acids of SEQ ID NO: 2, and an isolated nucleic acid molecule which hybridizes to a nucleic acid molecule comprising SEQ ID NO: 1. A nucleic acid molecule can include functional equivalents of natural nucleic acid molecules encoding a peptide, polypeptide or protein of the present invention. Functional equivalents of natural nucleic acid molecules can include, but are not limited to, natural allelic variants and modified nucleic acid molecules in which nucleotides have been inserted, deleted, substituted, and/or inverted in such a manner that such modifications do not substantially interfere with the nucleic acid molecule's ability to encode a molecule of the present invention. Said amino acid substitutions may be conservative or non-conservative.

Preferred functional equivalents include sequences capable of hybridizing under stringent conditions (i.e., sequences having at least about 70% identity), to at least a portion of an IG1 peptide, polypeptide or protein encoding nucleic acid molecule according to conditions described in Sambrook et al., (1989) Molecular Cloning—A Laboratory Manual, Cold Spring Harbor Laboratory Press. By stringent conditions it is meant that hybridization is carried in a buffer consisting of 0.1% SDS, 200 mM NaCl, 6 mM $Na_2HPO_4$, 2 mM EDTA at pH=6.8. More preferred functional equivalents include sequences capable of hybridizing under highly stringent conditions (i.e., sequences having at least about 90% identity), to at least a portion of an IG1 peptide, polypeptide or protein encoding nucleic acid molecule. By highly stringent conditions it is meant that hybridization is carried in a buffer consisting of 0.1% SDS, 10 mM NaCl, 0.3 mM $Na_2HPO_4$, 0.1 mM EDTA at pH=6.8. Nucleic acid molecules of the invention may encode a protein having at least about 50 or 60% amino acid sequence identity with the sequence set forth in SEQ ID NO: 2, preferably at least about 70 or 75%, more preferably at least about 80%, still more preferably at least about 85%, yet more preferably at least about 90%, even more preferably at least about 95% and most preferably at least about 98% sequence identity with the protein sequence set forth in SEQ ID NO: 2.

The present invention further includes the nucleic acid molecules operably linked to one or more expression control elements, including vectors comprising the isolated nucleic acid molecules. The invention further includes host cells transformed to contain the nucleic acid molecules of the invention and methods for producing a peptide, polypeptide or protein comprising the step of culturing a host cell transformed with a nucleic acid molecule of the invention under conditions in which the protein is expressed.

The invention further provides an isolated polypeptide selected from the group consisting of an isolated polypeptide comprising the amino acid sequence of SEQ ID NO: 2, an isolated polypeptide comprising a fragment of at least 6 amino acids of SEQ ID NO: 2, an isolated polypeptide comprising conservative amino acid substitutions of SEQ ID NO: 2 and an isolated polypeptide comprising naturally occurring amino acid sequence variants of SEQ ID NO: 2. Polypeptides of the invention also include polypeptides with an amino acid sequence having at least about 50 or 60% amino acid sequence identity with the sequence set forth in SEQ ID NO: 2, preferably at least about 70 or 75%, more preferably at least about 80%, still more preferably at least about 85%, yet more preferably at least about 90%, even more preferably at least about 95% and most preferably at least about 98% sequence identity with the protein sequence set forth in SEQ ID NO: 2.

This invention provides vectors comprising the nucleic acid constructs of the present invention as well as host cells, recombinant plant cells and transgenic plants comprising the vectors of the present invention. More particularly, this invention provides such cells and transgenic plants that are hemizygotic, heterozygotic or homozygotic for the nucleic acid constructs, wherein such plants can be monoploid, diploid or polyploid. It is an object of the present invention to provide such cells and transgenic plants wherein they express a single copy or multiple copies of one or more of the IG1, mutant IG1 (e.g., IG1-O or IG1-MUM), or IG1 ortholog (e.g., the rice IG1) protein products of the present invention. Cells or transgenic plants which express multiple copies of one of the IG1, mutant IG1, or IG1 ortholog proteins, or which express more than one of the IG1, mutant IG1, or IG1 ortholog proteins, may be desirable, for example, to produce male sterility for plant breeding or to generate androgenetic progeny in maize and other plant species.

The invention further provides nucleic acid probes for the detection of expression of IG1, or mutants, or homologs, or orthologs thereof, in plants which either have been genetically altered to express at least one of said proteins or which may naturally express IG1, or mutants, or homologs, or orthologs thereof.

The invention further provides the use of antibodies to IG1, or mutants, or homologs, or orthologs thereof to probe a biological sample or a tissue section for expression of IG1, or mutants, or homologs, or orthologs. Said biological sample or tissue section may be from a plant which has been genetically altered to express said peptide, polypeptide or protein or which may naturally express IG1, or mutants, or homologs, or orthologs. Thus, the present invention provides methods of identifying and isolating an ortholog of ig1 in a non-*Zea mays* plant species, said method comprising using at least one nucleic acid of the present invention as a nucleic acid probe.

The present invention also provides methods of modulating a plant cell comprising an ig1 gene, said method comprising the step of introducing into said plant cell an isolated polynucleotide according to the present invention, whereby the function and/or structure of the ig1 gene is modulated. More specifically, the present invention provides such methods wherein the isolated polynucleotide is a knock-out or knock-in construct.

The present invention also provides transgenic knock-out plants comprising disruption in the endogenous ig1 gene, wherein said disruption has been introduced into their genomes by homologous recombination with a DNA targeting construct such that the targeting construct is stably integrated in the genome of said plant, wherein the disruption of the ig1 gene results in a reduction of production of endogenous ig1 RNA levels.

The present invention also provides methods for down regulating ig1 RNA levels in a plant, said method comprising the of step introducing a vector provided by the present invention into plant tissue, wherein expression of said vector causes down-regulation of expression of ig1 RNA in said plant tissue.

Other objects, advantages and features of the present invention become apparent to one skilled in the art upon reviewing the specification and the drawings provided herein. Thus, further objects and advantages of the present invention will be clear from the description that follows.

BRIEF DESCRIPTION OF THE DRAWINGS

FIG. 6A. Mutant embryo sac (arrow) arrested at the one-nucleate stage of development.

FIG. 6B. Sibling embryo sac at the mature stage.

FIG. 9.

DETAILED DESCRIPTION

Figure 1:
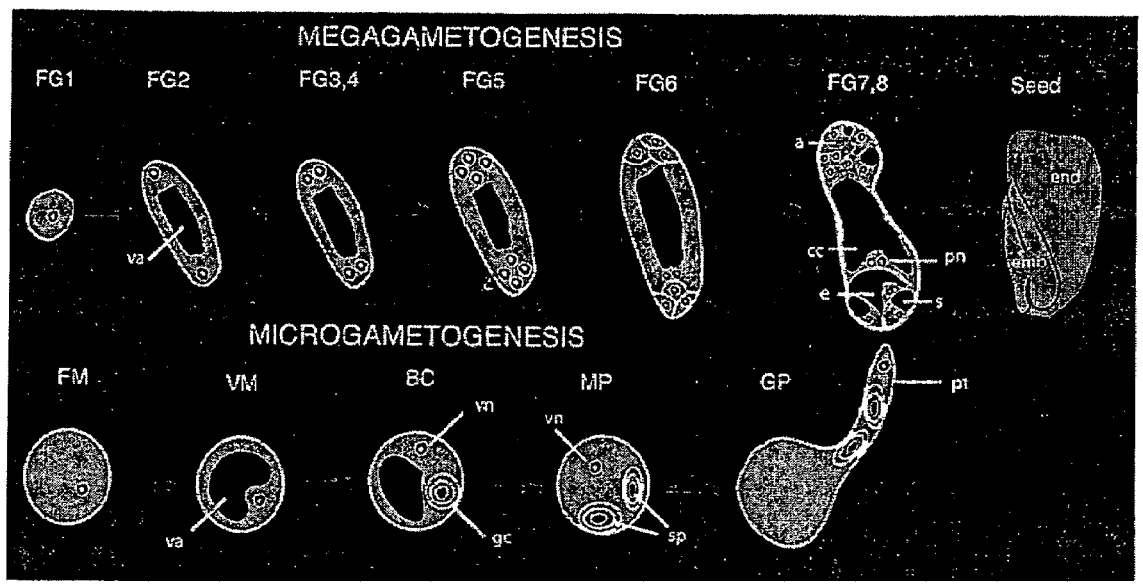
FIG. 1. Male and female gametophyte development. Key: a=antipodal cells; cc=central cell; pn=polar nuclei; e=egg cell; sy=synergid; end=endosperm; emb=embryo; va=vacuole; vn=vegetative cell; gc=generative cell; sp=sperm cells; pt=pollen tube. FG1-FG8=female gametophyte stage 1 to 8 (stages adapted from Christensen et al., 1997). FM=free microspore; VM=vacuolated microspore; BC=bicellular pollen; MP=mature pollen; and GP=germinating pollen.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

It will be appreciated from the above that the tools and methods of the present invention have application to all plants that produce gametes. Such plants include, but are not limited to, forage grasses, turf grasses, ornamental grasses, forage legumes, ground covers, vegetables, field crops (e.g., soybeans, corn, rice, cotton, tobacco, sorghum, field peas), trees and ornamental flowers.

I. Definitions

As used herein, the term "allele" refers to any of several alternative forms of a gene.

As used herein, the term "amino acid" refers to the aminocarboxylic acids that are components of proteins and peptides. The amino acid abbreviations are as follows:

| A (Ala) | C (Cys) | D (Asp) | E (Glu) | F (Phe) | G (Gly) |
|---------|---------|---------|---------|---------|---------|
| H (His) | I (Iso) | K (Lys) | L (Leu) | M (Met) | N (Asn) |
| P (Pro) | Q (Gln) | R (Arg) | S (Ser) | T (Thr) | V (Val) |
| W (Trp) | Y (Tyr) |         |         |         |         |

As used herein, the term "androgenesis" refers to male parthenogenesis, i.e., the development of a haploid embryo from a male nucleus.

As used herein, the term "androgenetic" refers to the haploid individual produced by androgenesis which contains in its cells the genome of the male gamete only.

As used herein, the term "crop plant" refers to any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food or food additives, smoking products, pulp production and wood production.

As used herein, the term "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "ectopic" refers to something occurring in an unusual place or in an unusual form or manner. For example, ectopic expression of a gene refers to having a gene expressed in a tissue or cell that would not normally express that gene.

As used herein, the term "endosperm" refers to a triploid structure resulting from the development of a fusion between two polar nuclei of the embryo sac and one of the sperm nucleus from the pollen found in many plant seeds. The endosperm frequently stores food materials, which are broken down during germination.

As used herein, the term "female" refers to a plant that produces ovules. Female plants generally produce seeds after fertilization. A plant designated as a "female plant" may contain both male and female sexual organs. Alternatively, the "female plant" may only contain female sexual organs either naturally (e.g., in dioecious species) or due to emasculation (e.g., by detasselling).

As used herein, the term "filial generation" refers to any of the generations of cells, tissues or organisms following a particular parental generation. The generation resulting from a mating of the parents is the first filial generation (designated as "F1" or "F1"), while that resulting from crossing of F1 individuals is the second filial generation (designated as "F2" or "$F_2$").

As used herein, the term "gamete" refers to a reproductive cell whose nucleus (and often cytoplasm) fuses with that of another gamete of similar origin but of opposite sex to form a zygote, which has the potential to develop into a new individual. Gametes are haploid and are differentiated into male and female.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, plant, or group of plants.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the term "male" refers to a plant that produces pollen grains. The "male plant" generally refers to the sex that produces gametes for fertilizing ova. A plant designated as a "male plant" may contain both male and female sexual organs. Alternatively, the "male plant" may only contain male sexual organs either naturally (e.g., in dioecious species) or due to emasculation (e.g., by removing the ovary).

As used herein, the term "mass selection" refers to a form of selection in which individual plants are selected and the next generation propagated from the aggregate of their seeds.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the terms "mutant" or "mutation" refer to a gene, cell, or organism with an abnormal genetic constitution that may result in a variant phenotype. For example, "a mutant ig1 gene" or "an ig1 gene with a mutation" refer to a gene with an alteration in the nucleotide sequence of the ig1 gene, such as ig1-O and ig1-mum.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. The term "nucleic acid" also encompasses polynucleotides synthesized in a laboratory using procedures well known to those skilled in the art.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the terms "ortholog" and "orthologue" refer to a nucleic acid or peptide sequence which functions similarly to a nucleic acid or peptide sequence from another species. For example, where one gene from one plant species has a high nucleic acid sequence similarity and codes for a protein with a similar function to another gene from another plant species, such genes would be orthologs.

As used herein, the term "ovule" refers to the female gametophyte, whereas the term "pollen" means the male gametophyte.

As used herein, the term "ovule-specific promoter" refers broadly to a nucleic acid sequence that regulates the expression of nucleic acid sequences selectively in the cells or tissues of a plant essential to ovule formation and/or function and/or limits the expression of a nucleic acid sequence to the period of ovule formation in a plant.

As used herein, the term "peptide" refers to a class of compounds of low molecular weight which yield two or more amino acids on hydrolysis and form the constituent parts of proteins. As used herein, an "oligopeptide" refers to any molecule that contains a small number (two to about 20) of amino-acid residues connected by peptide linkages.

As used herein, the term "phenotype" refers to the observable characters of an individual cell, cell culture, plant, or group of plants which results from the interaction between that individual's genetic makeup (i.e., genotype) and the environment.

As used herein, the term "plant" refers to whole plants, plant organs (e.g., leaves, stems, roots, etc.), seeds and plant cells and progeny of it. The class of plants that can be used in the methods of the invention is generally as broad as the class of higher plants amenable to transformation techniques, including both monocotyledonous and dicotyledonous plants.

As used herein, the term "plant line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "plant organ" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the terms "plant transcription unit" or "PTU" refer to a nucleic acid sequence encoding a promoter sequence, a coding sequence and a 3' termination sequence.

As used herein, the term "polypeptide" refers to a linear polymer of amino acids linked via peptide bonds. A polypeptide may be as short as 2 amino acids to virtually any length.

As used herein, the term "promoter" refers to a region of DNA involved in binding RNA polymerase to initiate transcription.

As used herein, the terms "protein," "peptide" or polypeptide" refer to amino acid residues and polymers thereof. Unless specifically limited, the terms encompass amino acids containing known analogues of natural amino acid residues that have similar binding properties as the reference amino acid and are metabolized in a manner similar to naturally occurring amino acid residues. Unless otherwise indicated, a particular amino acid sequence also implicitly encompasses conservatively modified variants thereof (e.g. conservative substitutions) as well as the sequence explicitly indicated. The term "polypeptide" also encompasses polypeptides synthesized in a laboratory using procedures well known to those skilled in the art.

As used herein, the term "recombinant" refers to a cell, tissue or organism that has undergone transformation with recombinant DNA. The original recombinant is designated as "R0" or "$R_0$." Selfing the R0 produces a first transformed generation designated as "R1" or "$R_1$."

As used herein, the term "self pollinated" or "self-pollination" means the pollen of one flower on one plant is applied (artificially or naturally) to the ovule (stigma) of the same or a different flower on the same plant.

As used herein, the term "signal sequence" refers to an amino acid sequence (the signal peptide) attached to the polypeptide which binds the polypeptide to the endoplasmic reticulum and is essential for protein secretion.

As used herein, the term "synthetic" refers to a set of progenies derived by intercrossing a specific set of clones or seed-propagated lines. A synthetic may contain mixtures of seed resulting from cross-, self-, and sib-fertilization.

As used herein, the term "transcript" refers to a product of a transcription process.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms, plants, and progeny of plants which have received a foreign or modified gene by one of the various methods of transformation, wherein the foreign or modified gene is from the same or different species than the species of the plant, or organism, receiving the foreign or modified gene.

As used herein, the term "transposition event" refers to the movement of a transposon from a donor site to a target site.

As used herein, the term "transposon" refers to a genetic element, including but not limited to segments of DNA or RNA that can move from one chromosomal site to another.

As used herein, the term "variety" refers to a subdivision of a species, consisting of a group of individuals within the species that are distinct in form or function from other similar arrays of individuals. As used herein, the terms "untranslated region" or "UTR" refer to any part of a mRNA molecule not coding for a protein (e.g., in eukaryotes the poly(A) tail).

As used herein, the term "vector" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO094/17810, published Aug. 18, 1994; International Patent Application No. WO094/23744, published Oct. 27, 1994). Examples of non-viral vectors include, but are not limited to, liposomes, polyamine derivatives of DNA, and the like.

II. Intermediate Gametophyte 1 (ig1)

Intermediate gametophyte (ig1) is an example of a mutant whose embryo sacs are viable but structurally variable (Lin 1978, 1981). ig1 embryo sacs undergo extra rounds of free nuclear divisions resulting in extra eggs, extra central cells, extra polar nuclei within central cells, and other defects (Lin 1978,1981; Huang and Sheridan, 1996). The exact number and placement of nuclei at cellularization is variable in ig1. The phenotypes of ig1 embryo sacs suggest a position-based determination of cellular identity. The ability of the extra cells and nuclei to function as egg cells or polar nuclei, for example, may depend on their position in the embryo sac. Many of these defective embryo sacs give rise to abnormal seeds, displaying polyembryony, heterofertilization, haploid embryos, miniature endosperms, and early abortion (Kermicle, 1971). However, because ig1 embryo sacs are viable, homozygous lines can be established. These homozygous plants have normal vegetative development and reproductive morphology but in some genetic backgrounds are male sterile, failing to shed pollen or even exert anthers in most plants (Kermicle, 1994). Many of the aspects of the ig1 phenotype are consistent with reduced negative regulation of nuclear divisions in the embryo sac. ig1 is unique among published female gametophyte mutants, in having extra rounds of nuclear division prior to cellularization.

One function of the ig1 gene is to restrict the embryogenic potential of cells that lack one of the two parental genomes. ig1 mutant embryo sacs produce haploid progeny, of both maternal and paternal origin, at a higher rate than wild type (Kermicle, 1969). The increased frequency of androgenesis (production of progeny with only a paternal genomic contribution) when ig1 is the female parent has been exploited agronomically in maize. Haploids can be generated to produce homozygous lines rapidly, and nuclear genotypes can be combined with different cytoplasms, such as those conditioning male sterility (Albertsen and Trimnell, 1990; Kindiger and Hamann, 1993; Kermicle, 1994). This is accomplished while simultaneously removing the ig1 mutation, because it is only present in the female parent. This eliminates the need for recurrent backcrossing and thus dramatically reduces the time needed to transfer the germplasm of new elite lines into a male sterile cytoplasm. The ability either to identify or engineer this phenotype in other agronomically important crops that use cytoplasmic male sterile lines for hybrid production would improve the efficiency of breeding in these species.

III. Nucleic Acids

A. Promoters

An inducible promoter is a promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

A viral promoter is a promoter with a DNA sequence substantially similar to the promoter found at the 5' end of a viral gene. For example, a typical viral promoter is found at the 5' end of the gene coding for the p2I protein of MMTV described by Huang et al., Cell 27:245 (1981).

A synthetic promoter is a promoter that was chemically synthesized rather than biologically derived. Usually synthetic promoters incorporate sequence changes that optimize the efficiency of RNA polymerase initiation.

A constitutive promoter is a promoter that promotes the expression of a gene product throughout an organism, such as a plant. Examples of constitutive promoters include the cauliflower mosaic virus 35S and 19S promoters (for example, Poszkowski et al., EMBO J. 3: 2719 (1989); Odell et al., Nature 313:810 (1985)); and the maize ubiquitin-1 promoter (for example, U.S. Pat. Nos. 5,510,474; 5,614,399; 6,020,190 and 6,054,574).

A temporally regulated promoter is a promoter where the rate of RNA polymerase binding and initiation is modulated at a specific time during development. Examples of temporally regulated promoters are given in, for example, Chua et al., Science, 244:174-181 (1989).

A spatially regulated promoter is a promoter where the rate of RNA polymerase binding and initiation is modulated in a specific structure of the organism such as the leaf, stem, seed or root. Examples of spatially regulated promoters are given in Chua et al,. Science 244:174-181 (1989). Such tissue-specific or organ-specific promoters are well known in the art and include but are not limited to seed-specific promoters, organ-primordia specific promoters, stem-specific promoters, leaf specific promoters, mesophyl-specific promoters (such as the light-inducible Rubisco promoters), root-specific promoters, tuber-specific promoters, vascular tissue specific promoters, stamen-selective promoters, dehiscence zone specific promoters and the like. The most preferred promoters for use in the instant invention will be most active in seed, fruit and tuber.

A spatiotemporally regulated promoter is a promoter where the rate of RNA polymerase binding and initiation is modulated in a specific structure of the organism at a specific time during development. An example of a typical spatiotemporally regulated promoter is the EPSP synthase-35S promoter described by Chua et al,. Science 244:174-181 (1989).

There are many excellent examples of suitable promoters to drive pollen-specific expression in plants. Pollen-specific promoters have been identified in many plant species such as maize, rice, tomato, tobacco, *Arabidopsis, Brassica*, and others (Odell, T. O., et al. (1985) Nature 313:810-812; Marrs, K. A., et al, (1993) Dev Genet, Vol. 14/1:27-41; Kim, (1992) Transgenic Res, Vol. 1/4:188-94; Carpenter, J. L., et al. (1992) Plant Cell Vol. 4/5:557-71; Albani, D. et al., (1992) Plant J. 2/3:331-42; Rommens, C. M., et al. (1992), Mol. Gen. Genet., Vol. 231/3:433-41; Kloeckener-Gruissem, et al., (1992) Embo J, Vol. 11/1: 157-66; Hamilton, D. A. et al., (1992), Plant Mol Biol, Vol. 18/2:211-18; Kyozuka, J., et al. (1991), Mol. Gen. Genet., Vol. 228/1-2:40-8; Albani, D. et. al (1991) Plant Mol Biol Vol. 16/4:501-13; Twell, D. et al. (1991) Genes Dev. 5/3:496-507; Thorsness, M. K. et al., (1991) Dev. Biol Vol. 143/1:173-84; McCormick, S. et al. (1991) Symp Soc Exp Biol Vol. 45:229-44; Guerrero, F. D. et al. (1990) Mol Gen Genet Vol 224/2:161-8; Twell, D. et al., (1990) Development Vol. 109/3:705-13; Bichler, J. et al. (1990), Eur J Biochem Vol. 190/2:415-26; van Tunen, et al. (1990), Plant Cell Vol 2/5:393-401; Siebertz, B. et al. (1989) Plant Cell Vol 1/10:961-8; Sullivan, T. D. et al., (1989) Dev Genet Vol 10/6:412-24; Chen, J. et al. (1987), Genetics Vol 116/3:469-77). Several other examples of pollen-specific promoters can be found in GenBank. Additional promoters are also provided in U.S. Pat. Nos. 5,086,169; 5,756,324; 5,633,438; 5,412,085; 5,545,546 and 6,172,279.

There are also several other eukaryotic sex-specific promoters suitable for use in the instant invention. Examples include: the mouse spermatocyte-specific Pgk-2 promoter (Ando et al. (2000) Biochem. Biophys. Res. Comm. 272/1: 125-8); the PACAP testis-specific promoter (Daniel et al. (2000) Endocrinology, 141/3:1218-27); the mouse mSP-10 spermatid-specific promoter (Reddi et al. (1999) Biology of Reproduction, 61/5:1256-66); the mouse sperm-specific promoter (Ramara et al. (1998) J. Clin. Invest. 102/2:371-8); the mouse and rat H1t promoters (vanWert et al. (1996) J. Cell. Biochem. 60/3:348-62); the human PRM1, PRM2 and TNP2 spermatid-specific promoters (Nelson et al. (1995) DNA Sequence 5/6:329-37); the *Drosophila* exu sex-specific promoter (Crowley et al. (1995) Molec. Gen. Genet. 248/3:370-4); the mouse testis ACE promoter (Zhou et al. (1995) Dev. Genet. 16/2:201-9); the rat GHRH spermatogenic-specific promoter (Srivastava et al. (1995) Endocrinology 136/4: 1502-8); the *Drosophila* testis-specific promoter (Lankenau et al. (1994) Mol. Cell. Biol. 14/3:1764-75); the spermatocyte-specific hst70 gene promoter (Widlak et al. (1994) Acta Biochim. Polonica 41/2:103-5); and the mouse Prm-1 spermatid-specific promoter (Zambrowicz et al. (1993) Proc. Nat'l. Acad. Sci. USA 90/11:5071-5).

Expression of seed-specific genes has been studied in great detail (see reviews, for example, by Goldberg et al., Cell 56:149-160 (1989) and Higgins et al., Ann. Rev. Plant Physiol. 35:191-221 (1984)). Promoter analysis of seed-specific genes is reviewed in Goldberg et al., Cell 56: 149-160 (1989) and Thomas, Plant Cell 5: 1401-1410 (1993). Research indicates that no plant gene is more tightly regulated in terms of spatial expression than those encoding seed storage proteins.

Many seed storage protein genes have been cloned from diverse plant species, and their promoters have been analyzed in detail (Thomas, Plant Cell 5: 1401-1410 (1993)). There are currently numerous examples of seed-specific expression of seed storage protein genes in transgenic plants. See, for example, b-phaseolin (Sengupta-Gopalan et al., Proc. Natl. Acad, Sci. USA 82:3320-3324 (1985); Hoffman et al., Plant Mol. Biol. 11, 717-729 (1988)); bean lectin (Voelker et al., EMBO J. 6: 3571-3577 (1987)); soybean lectin (Okamuro et al,. Proc. Natl. Acad. Sci. USA 83:8240-8244 (1986)); soybean Kunitz trypsin inhibitor (Perez-Grau et al., Plant Cell 1:095-1109 (1989)); soybean b-conglycinin (Beachy et al., EMBO J. 4:3047-3053 (1985); pea vicilin (Higgins et al., Plant Mol. Biol. 11:683-695 (1988)); pea convicilin (Newbigin et al., Planta 180:461-470 (1990)); pea legumin (Shirsat et al., Mol. Gen. Genetics 215:326-331 (1989)); rapeseed napin (Radke et al., Theor. Appl. Genet. 75:685-694(1988)); maize 18 kD oleosin (Lee et al., Proc Natl. Acad. Sci. USA 888: 6181-6185 (1991)); barley b-hordein (Marris et al., Plant Mol. Biol. 10:359-366 (1988); wheat glutenin (Colot et al., EMBO J. 6:3559-3564 (1987)). For additional sources of seed-specific promoters, see, for example, U.S. Pat. Nos. 5,623,067; 6,100,450; 6,177,613; 6,225,529; 6,342,657 and 6,403,371; Knutzon et al,. Proc. Natl. Acad. Sci. USA 89:2624 (1992); Bustos et al., EMBO J. 10:1469 (1991), Lam and Chua, Science 248:471(1991); Stayton et al., Aust. J. Plant. Physiol. 18:507 (1991), each of which is incorporated by reference in its entirety. Moreover, seed-specific promoter genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *B. napus* seeds (see, for example, Vandekerckhove et al., Bio/Technology 7:929-932 (1989)); bean lectin and bean b-phaseolin promoters to express luciferase (see, for example, Riggs et al., Plant Sci. 63:47-57 (1989)); and wheat glutenin promoters to express chloramphenicol acetyl transferase (see, for example, Colot et al., EMBO J. 6:3559-3564 (1987)).

B. Transgenes and Heterologous Nucleic Acids

There are numerous examples of genes successfully introduced into plants using recombinant DNA methodologies including, but not limited to, those coding for the following traits: seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554,798; Powell et al., Science 232: 738-743 (1986); Kaniewski et al., Bio/Tech. 8:750-754 (1990); Day et al., Proc. Natl. Acad. Sci. USA 88:6721-6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597,946; Hilder et al., Nature 330:160-163; Johnson et al., Proc. Natl. Acad. Sci. USA, 86:9871-9875 (1989); Perlak et al., Bio/Tech. 8:939-943 (1990)); lectins (U.S. Pat. No. 5,276,269); and flower color (Meyer et al., Nature 330:677-678 (1987); Napoli et al., Plant Cell 2:279-289 (1990); van der Krol et al., Plant Cell 2:291-299 (1990)).

C. Site-Specific Recombination Systems

Methods and constructs for targeting of DNA sequences for insertion into a particular DNA locus, while enabling removal of randomly inserted DNA sequences that occur as a by-product of transformation procedures, are described in U.S. Pat. Nos. 5,527,695 and 6,114,600. One manner of removing these random insertions is to utilize a site-specific recombinase system. In general, a site-specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site-specific recombinase systems can be used, including but not limited to the Cre/lox system of bacteriophage P1, the FLP/FRT system of yeast, the Gin recombinase of phage Mu, the Pin recombinase of *E. coli*, and the R/RS system of the pSR1 plasmid. The two preferred site-specific recombinase systems are the bacteriophage P1 Cre/lox and the yeast FLP/FRT systems. In these systems a recombinase (Cre or FLP) will interact specifically with its respective site-specific recombination sequence (lox or FRT respectively) to invert or excise the intervening sequences. The sequence for each of these two systems is relatively short (34 bp for lox and 47 bp for FRT). Currently the FLP/FRT system of yeast is the preferred site-specific recombinase system since it normally functions in a eukaryotic organism (yeast), and is well characterized. It is thought that the eukaryotic origin of the FLP/FRT system allows the FLP/FRT system to function more efficiently in eukaryotic cells than the prokaryotic site-specific recombinase systems.

The FLP/FRT recombinase system has been demonstrated to function efficiently in plant cells. Experiments on the performance of the FLP/FRT system in both maize and rice protoplasts indicates that FRT site structure, and amount of the FLP protein present, affects excision activity. In general, short incomplete FRT sites leads to higher accumulation of excision products than the complete full-length FRT sites. Site-specific recombination systems can catalyze both intra- and intermolecular reactions in maize protoplasts, indicating that the system can be used for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

D. Vectors

Expression Units to Express Exogenous DNA in a Plant

As provided above, several embodiments of the present invention employ expression units (or expression vectors or systems) to express an exogenously supplied nucleic acid sequence in a plant. Methods for generating expression units/systems/vectors for use in plants are well known in the art and can readily be adapted for use in the instant invention. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumafacians*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit-specific promoters, Ap3 promoter, heat shock promoters, seed-specific promoters, etc. can also be used.

Either a gamete-specific promoter, a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., *EMBO J* 3:835-846 (1984)) or the nopaline synthase signal (Depicker et al., Mol. and Appl. Genet. 1:561-573 (1982)).

The resulting expression unit is ligated into or otherwise constructed to be included in a vector that is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as ampicillin, kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

The sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., FEBS Lett. 405(2):129-132 (1997); *Arabidopsis thaliana* Database, http://genome.www-.stanford.edu/*Arabidopsis*). For a discussion of the analysis of gene-expression patterns derived from large EST databases, see, e.g., M. R. Fannon, TIBTECH 14:294-298 (1996).

Biologically compatible fluorescent protein probes, particularly the self-assembling green fluorescent protein (GFP) from the jellyfish *Aequorea Victoria*, have revolutionized research in cell, molecular and developmental biology because they allow visualization of biochemical events in living cells (Murphy et al., Curr. Biol. 7(11):870-876 (1997); Grebenok et al., Plant J. 11(3):573-586 (1997); Pang et al., Plant Physiol. 112(3) (1996); Chiu et al., Curr. Biol. 6(3):325-330 (1996); Plautz et al., Gene 173(1):83-87 (1996); Sheen et al., Plant J. 8(5):777-784 (1995)).

Site-directed mutagenesis has been used to develop a more soluble version of the codon-modified GFP called soluble-modified GFP (smGFP). When introduced into *Arabidopsis*, greater fluorescence was observed when compared to the codon-modified GFP, implying that smGFP is 'brighter' because more of it is present in a soluble and functional form (Davis et al., Plant Mol. Biol. 36(4):521-528 (1998)). By fusing genes encoding GFP and beta-glucuronidase (GUS), researchers were able to create a set of bifunctional reporter constructs which are optimized for use in transient and stable expression systems in plants, including *Arabidopsis* (Quaedvlieg et al., Plant Mol. Biol. 37(4):715-727 (1998)).

Berger et al. (Dev. Biol. 194(2):226-234 (1998)) report the isolation of a GFP marker line for *Arabidopsis* hypocotyl epidermal cells. GFP-fusion proteins have been used to localize and characterize a number of *Arabidopsis* genes, including geranylgeranyl pyrophosphate (GGPP) (Zhu et al., Plant Mol., Biol. 35(3):331-341 (1997).

IV. Transformation

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including alfalfa. See, for example, Wang et al., Australian Journal of Plant Physiology 23(3): 265-270 (1996); Hoffman et al., Molecular Plant-Microbe Interactions 10(3): 307-315 (1997); and, Trieu et al., Plant Cell Reports 16:6-11 (1996).

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method, including alfalfa (U.S. Pat. No. 5,324,646) and clover (Voisey et al., Biocontrol Science and Technology 4(4): 475-481 (1994); Quesbenberry et al., Crop Science 36(4): 1045-1048 (1996); Khan et al., Plant Physiology 105 (1): 81-88 (1994); and, Voisey et al., Plant Cell Reports 13(6): 309-314 (1994)).

Developed by ICI Seeds Inc. (Garst Seed Company) in 1993, WHISKERS™ is an alternative to other methods of inserting DNA into plant cells (e.g., the Biolistic® Gene Gun, *Agrobacterium tumefaciens*, the "Shotgun" Method, etc.); and it consists of needle-like crystals ("whiskers") of silicon carbide. The fibers are placed into a container along with the plant cells, then mixed at high speed, which causes the crystals to pierce the plant cell walls with microscopic "holes" (passages). Then the new DNA (gene) is added, which causes the DNA to flow into the plant cells. The plant cells then incorporate the new gene(s); and thus they have been genetically engineered.

The essence of the WHISKERS™ technology is the small needle-like silicon carbide "whisker" (0.6 microns in diameter and 5-80 microns in length) which is used in the following manner. A container holding a "transformation cocktail" composed of DNA (e.g., agronomic gene plus a selectable marker gene), embryogenic corn tissue, and silicon carbide "whiskers" is mixed or shaken in a robust fashion on either a dental amalgam mixer or a paint shaker. The subsequent collisions between embryogenic corn cells and the sharp silicon carbide "whiskers" result in the creation of small holes in the plant cell wall through which DNA (the agronomic gene) is presumed to enter the cell. Those cells receiving and incorporating a new gene are then induced to grow and ultimately develop into fertile transgenic plants.

Silicon carbide "whisker" transformation has now produced stable transformed calli and/or plants in a variety of plants species such as *Zea mays*. See, for example, U.S. Pat. Nos. 5,302,523 and 5,464,765, each of which is incorporated herein by reference in their entirety; Frame et al., The Plant Journal 6: 941-948 (1994); Kaeppler et al., Plant Cell Reports 9:415-418 (1990); Kaeppler et al., Theoretical and Applied Genetics 84:560-566 (1992); Petolino et al., Plant Cell Reports 19(8):781-786 (2000); Thompson et al., Euphytica 85:75-80 (1995); Wang et al., In Vitro Cellular and Developmental Biology 31:101-104 (1995); Song et al., Plant Cell Reporter 20:948-954 (2002); Petolino et al., Molecular Methods of Plant Analysis, In Genetic Transformation of Plants, Vol. 23, pp. 147-158, Springer-Verlag, Berlin (2003). Other examples include *Lolium multiflorum, Lolium perenne, Festuca arundinacea, Agrostis stolonifera* (Dalton et al., Plant Science 132:31-43 (1997)), *Oryza sativa* (Nagatani et al., Biotechnology Techniques 11:471-473 (1997)), and *Triticum aestivum* and *Nicotiana tobacum* (Kaeppler et al., Theoretical and Applied Genetics 84:560-566 (1992)). Even Chlamydomonas (see, for example, Dunahay, T. G., Biotechniques 15:452-460 (1993)) can be transformed with a "whiskers" approach. As it is currently practiced on higher plants, the "whisker" system is one of the least complex ways to transform some plant cells.

Genes successfully introduced into plants using recombinant DNA methodologies include, but are not limited to, those coding for the following traits: seed storage proteins, including modified 7S legume seed storage proteins (see, for example, U.S. Pat. Nos. 5,508,468, 5,559,223 and 5,576, 203); herbicide tolerance or resistance (see, for example, De Greef et al., Bio/Technology 7:61 (1989); U.S. Pat. Nos. 4,940,835; 4,769,061; 4,975,374; Marshall et al.(1992) Theor. Appl. Genet. 83, 435; U.S. Pat. Nos. 5,489,520; 5,498, 544; 5,554,798; Powell et al., Science 232:738-743 (1986); Kaniewski et al,. Bio/Tech. 8:750-754 (1990)); Day et al., Proc. Natl. Acad. Sci. USA 88:6721-6725 (1991)); phytase (see, for example, U.S. Pat. No. 5,593,963); resistance to bacterial, fungal, nematode and insect pests, including resistance to the lepidoptera insects conferred by the Bt gene (see, for example, U.S. Pat. Nos. 5,597,945 and 5,597,946; Johnson et al., Proc. Natl. Acad. Sci. USA, 86:9871-9875 (1989); Perlak et al., *Bio/Tech.* 8:939-943 (1990)); lectins (U.S. Pat. No. 5,276,269); flower color (Meyer et al., Nature 330:677-678 (1987); Napoli et al., Plant Cell 2:279-289 (1990); van der Krol et al., Plant Cell 2:291-299 (1990)); Bt genes (Voisey et al., supra); neomycin phosphotransferase II (Quesbenberry et al., supra); the pea lectin gene (Diaz et al., Plant Physiology 109(4): 1167-1177 (1995); Eijsden et al., Plant Molecular Biology 29(3):431-439 (1995)); the auxin-responsive promoter GH3 (Larkin et al., Transgenic Research 5(5):325-335 (1996)); seed albumin gene from sunflowers (Khan et al., Transgenic Research 5(3):179-185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra), each of which is expressly incorporated herein by reference in their entirety.

For certain purposes, different antibiotic or herbicide selection markers may be preferred. Selection markers used routinely in transformation include the nptII gene which confers resistance to kanamycin and related antibiotics (see, for example, Messing & Vierra, Gene 19: 259-268 (1982); Bevan et al., Nature 304:184-187 (1983)), the bar gene which confers resistance to the herbicide phosphinothricin (White et al., Nucl Acids Res 18: 1062 (1990), Spencer et al., Theor Appl Genet 79: 625-631(1990)), and the dhfr gene, which confers resistance to methotrexate (Bourouis et al., EMBO J. 2(7): 1099-1104 (1983)).

Transgenic alfalfa plants have been produced using a number of different genes isolated from both alfalfa and non-alfalfa species including, but not limited to, the following: the promoter of an early nodulin gene fused to the reporter gene gusA (Bauer et al., The Plant Journal 10(1):91-105 (1996)); the early nodulin gene (Charon et al., Proc. Natl. Acad. of Sci. USA 94(16):8901-8906 (1997); Bauer et al., Molecular Plant-Microbe Interactions 10(1):39-49 (1997)); NADH-dependent glutamate synthase (Gantt, The Plant Journal 8(3): 345-358 (1995)); promoter-gusA fusions for each of three lectin genes (Bauchrowitz et al., The Plant Journal 9(1):31-43 (1996)); the luciferase enzyme of the marine soft coral *Renilla reniforms* fused to the CaMV promoter (Mayerhofer et al., The Plant Journal 7(6): 1031-1038 (1995)); Mn-superoxide dismutase cDNA (McKersie et al., Plant Physiology 111(4): 1177-1181 (1996)); synthetic cryIC genes encoding a *Bacillus thuringiensis* delta-endotoxin (Strizhov et al., Proc. Natl. Acad. Sci. USA 93(26):15012-15017 (1996)); glucanse (Dixon et al., Gene 179(1):61-71 (1996); a senescence gene (U.S. Pat. No. 5,689,042).

Genetic transformation has also been reported in numerous forage and turfgrass species (Conger B. V., Genetic Transformation of Forage Grasses in Molecular and Cellular Technologies for Forage Improvement, CSSA Special Publication No. 26, Crop Science Society of America, Inc. E. C. Brummer et al. Eds. 1998, pages 49-58). These include, but are not limited to, orchardgrass (*Dactylis glomerata* L.), tall fescue (*Festuca arundinacea* Schreb.) red fescue (*Festuca rubra* L.), meadow fescue (*Festuca pratensis* Huds.) perennial ryegrass (*Lolium perenne* L.) creeping bentgrass (*Agrostis palustris* Huds.) and redtop (*Agrostis alba* L.).

V. Hemizygosity

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Assuming normal hemizygosity, selfing will result in maximum genotypic segregation in the first selfed recombinant generation, also known as the R1 or $R_1$ generation. The R1 generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few R1 plants need to be grown to find at least one resistance phenotype (U.S. Pat. Nos. 5,436,175 and 5,776,760).

As mentioned above, self-pollination of a hemizygous transgenic regenerated plant should produce progeny equivalent to an F2 in which approximately 25% should be homozygous transgenic plants. Self-pollination and testcrossing of the F2 progeny to non-transformed control plants can be used to identify homozygous transgenic plants and to maintain the line. If the progeny initially obtained for a regenerated plant were from cross-pollination, then identification of homozygous transgenic plants will require an additional generation of self-pollination (U.S. Pat. No. 5,545,545).

VI. Disabling Genes

It may be desirable to disable certain plant genes to gain the expression of the transgene and/or to obtain the desired protein produced as a result of the expression of the transgene. For example, in the instant invention, it may be desirable to disable certain enzymes that are native to the transgenic plant, for example one or more specific plant transferases. Methods of disabling genes are well known to those of ordinary skill in the art.

For example, an effective disabling modification is the introduction of a single nucleotide deletion occurring at the beginning of a gene that would produce a translational reading frameshift. Such a frameshift would disable the gene, resulting in non-expressible gene product and thereby disrupting functional protein production by that gene. If the unmodified gene encodes a protease, for example, protease production by the gene could be disrupted if the regulatory regions or the coding regions of the protease gene are disrupted.

In addition to disabling genes by deleting nucleotides, causing a transitional reading frameshift, disabling modifications would also be possible by other techniques well known to those of ordinary skill, including insertions, substitutions, inversions or transversions of nucleotides within the gene's DNA that would effectively prevent the formation of the protein encoded by the DNA.

It is also within the capabilities of one skilled in the art to disable genes by the use of less specific methods. Examples of less specific methods would be the use of chemical mutagens such as hydroxylamine or nitrosoguanidine or the use of radiation mutagens such as gamma radiation or ultraviolet radiation to randomly mutate genes. Such mutated strains could, by chance, contain disabled genes such that the genes were no longer capable of producing functional proteins for any one or more of the domains. The presence of the desired disabled genes could be detected by routine screening techniques. For further guidance, see, for example, U.S. Pat. No. 5,759,538.

VII. Down Regulation

Down-regulation of expression of a target gene may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal MRNA transcribed from the "sense" strand of the target gene. See, for example, Smith et al, (1988) Nature 334:724-726; Zhang et al,(1992) The Plant Cell 4:1575-1588, English et al., (1996) The Plant Cell 8:179-188. Antisense technology is also reviewed in Bourque, (1995), Plant Science 105:125-149, and Flavell, (1994) PNAS USA 91:3490-3496. Methods for inhibiting expression in plants using antisense constructs, including generation of antisense sequences in situ are well known to those of ordinary skill in the art and are also described, for example, in U.S. Pat. Nos. 5,107,065; 5,254,800; 5,356,799; 5,728,926; and 6,184,439.

"Co-suppression" refers to the production of sense RNA transcripts capable of suppressing the expression of identical or substantially similar foreign or endogenous genes (U.S. Pat. No. 5,231,020). An alternative is to use a copy of all or part of the target gene inserted in sense, that is the same, orientation as the target gene, to achieve reduction in expression of the target gene by co-suppression. See, for example, van der Krol et al., (1990) The Plant Cell 2:291-299; Napoli et al., (1990) The Plant Cell 2:279-289; Zhang et al., (1992) The Plant Cell 4:1575-1588, and U.S. Pat. No. 5,231,020. Further refinements of gene silencing or co-suppression technology may be found in WO095/34668 (Biosource); Angell & Baulcombe (1997) The EMBO Journal 16(12):3675-3684; and Voinnet & Baulcombe (1997) Nature 389, pg 553.

The complete sequence corresponding to the coding sequence (in reverse orientation for anti-sense) need not be used. For example fragments of sufficient length, such as SEQ ID NO: 1, may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Generally, the transcribed nucleic acid may represent a fragment of an ig1 gene, such as including a nucleotide sequence provided in SEQ ID NO: 1, or the complement thereof, or may be a mutant, ortholog, derivative, variant or allele thereof, in similar terms as discussed above in relation to alterations being made to an ig1 coding sequence and the homology of the altered sequence. The homology may be sufficient for the transcribed anti-sense RNA to hybridise with nucleic acid within cells of the plant, though irrespective of whether hybridisation takes place the desired effect is down-regulation of gene expression.

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See, for example, H. E. Moser et al., Science 238:645-650 (1987) and M. Cooney et al., Science 241:456-459 (1988)). Regions in the control sequences containing stretches of purine bases are particularly attractive targets. Triple helix formation along with photocrosslinking is described, e.g., in D. Praseuth et al., Proc. Nat'l Acad. Sci. USA 85:1349-1353 (1988).

VIII. Knock-Ins and Knock-Outs

As used herein, the term "knock-in" refers to a cell, tissue or organism that has had a gene introduced into its genome, wherein the gene can be of exogenous or endogenous origin. Generally, if the introduced gene is endogenous in origin, it will be a modified gene. An introduced gene that is exogenous in origin can be in its wild-type form or in a modified form.

As used herein, a "knock-out" refers to a cell, tissue or organism in which there is partial or complete suppression of the expression of an endogenous gene (e.g., based on deletion of at least a portion of the gene, replacement of at least a portion of the gene with a second sequence, introduction of stop codons, the mutation of bases encoding critical amino acids, or the removal of an intron junction, etc.). The targeted gene can be partially or completely suppressed by disruption, inactivation or deletion. Said partial suppression may also be referred to herein as a "knock-down." Knock-outs can be performed using both in vitro and in vivo recombination techniques. In order to study gene functions, usually the cell, tissue or organism is genetically engineered with specified wild-type alleles replaced with mutated ones. Knock-outs can be made using homologous recombination between the target gene and a piece of cloned DNA to insert a piece of "junk" DNA into the gene desired to be disrupted. If the organism is haploid, then this technique will result in that organism's only copy of the gene being knocked out. If it is diploid, then only one of the two alleles will be knocked out, and it will be necessary to do conventional breeding to produce a diploid organism that has two copies of the gene knocked out.

IX. Over-Expression

"Overexpression" refers to the production of a gene product in transgenic organisms that exceeds levels of production in normal or non-transformed organisms. In the present invention, over-expression of ig1 may be achieved by introduction of the nucleotide sequence of ig1 in a sense orientation.

Thus, the present invention provides a method of influencing a physical, e.g. flowering characteristic of a plant, the method including causing or allowing expression of the product (polypeptide or nucleic acid transcript) encoded by heterologous nucleic acid according to the invention from that nucleic acid within cells of the plant.

Methods of over-expressing genes are generally known by those skilled in the art. For examples of producing cells which over-express specific genes, see, for example, U.S. Pat. Nos. 5,905,146; 5,849,999; 5,859,311; 5,602,309; 5,952,169 and 5,772,997; Saito et al., "Modulation of Cystein Biosynthesis in Chloroplasts of Transgenic Tobacco Overexpressing Cysteine Synthase [O-Acetylserine(thiol)-lyase]", Plant Physiology (1996) 106:887-895.

X. Double Stranded RNA Interference (dsRNAi)

Reduction or inhibition of a gene can also be accomplished through the use of a RNA interference (RNAi). As is well known to those skilled in the art, this is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., Nature (1998) 391(19):306-311; Timmons et al., Nature (1998) 395:854; Montgomery et al., TIG (1998) 14(7):255-258; David R. Engelke, Ed., RNA Interference (RNAi) Nuts & Bolts of RNAi Technology, DNA Press (2003); Gregory J. Hannon, Ed., and RNAi A Guide to Gene Silencing, Cold Spring Harbor Laboratory Press (2003). For plant-specific information on dsRNAi see, for example, WO 99/53050; and WO 99/49029. Therefore, the present invention also includes methods of silencing genes by using RNAi technology.

XI. Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, *In Hybridization of Crop Plants.*

XII. Genetic Probes

The present invention further provides methods of recognizing variations in the DNA sequence of *Zea mays* ig1 as well as for detecting the gene or its homologs or orthologs in other plant genera, species, strains, varieties or cultivars. One method involves the introduction of a nucleic acid molecule (also known as a probe or nucleic acid probe) having a sequence identical or complementary to at least a portion of ig1 (SEQ ID NO: 1) of the invention under sufficient hybridizing conditions as would be understood by those in the art, such as the moderately stringent or highly stringent hybridization conditions as described elsewhere within the instant description. Said probe would share identity with the DNA sequence of SEQ ID NO: 1 over at least about 10 contiguous nucleic acid residues. Preferably, said identity would be over at least about 25 or 30 contiguous nucleic acid residues. More preferably, said identity would be over at least about 40 or 50 contiguous nucleic acid residues. Even more preferably, said identity would be over at least about 60 or 75 contiguous nucleic acid residues. Still more preferably, said identity would be over at least about 100 or 150 contiguous nucleic acid residues. Yet more preferably, said identity would be over at least about 200 or 250 contiguous nucleic acid residues. Most preferably, said identity would be over at least about 300 contiguous nucleic acid residues or would math the entire open reading frame of SEQ ID NO: 1 or its complement.

Another method of recognizing DNA sequence variation is direct DNA sequence analysis by multiple methods well known in the art. Another embodiment involves the detection of DNA sequence variation in IGI proteins as represented by different plant genera, species, strains, varieties or cultivars. Another embodiment involves using said nucleic acid probes for the detection of ig1 sequences in a sample or tissue section using in situ hybridization according to any method known to those of skill in the art. The ig1 sequence used for the probe can be from any plant for which the presence of ig1 has been determined. A particularly good probe for a monocotyledonous plant would be that coding for the IG1 of maize. In one embodiment, the sequence will bind specifically to one allele of a IG1-encoding gene, or a fragment thereof, and in another embodiment will bind to multiple alleles. Such detection methods include the polymerase chain reaction, restriction fragment length polymorphism (RFLP) analysis and single stranded conformational analysis.

Diagnostic probes useful in such assays of the invention include antibodies to IG1 proteins. The antibodies to IG1 may be either monoclonal or polyclonal, produced using standard techniques well known in the art (See Harlow & Lane's *Antibodies: A Laboratory Manual*, Cold Spring Harbor Laboratory Press, 1988). They can be used to detect IGI, or a homolog or ortholog thereof, protein by binding to the protein and subsequent detection of the antibody-protein complex by ELISA, Western blot or the like. The IG1 sequence used to elicit these antibodies can be any of the IG1 variants discussed herein, including IG1-O and IG1-MUM. Antibodies are also produced from peptide sequences of IG1 using standard techniques in the art (See *Protocols in Immunology*, John Wiley & Sons, 1994). Fragments of the monoclonals or the polyclonal antisera which contain the immunologically significant portion can also be prepared.

Assays to detect or measure IG1 polypeptide in a biological sample with an antibody probe may be based on any available format. For instance, in immunoassays where IG1 polypeptides are the analyte, the test sample, typically a biological sample, is incubated with anti-IG1 antibodies under conditions that allow the formation of antigen-antibody complexes. Various formats can be employed, such as "sandwich" assay where antibody bound to a solid support is incubated with the test sample; washed, incubated with a second, labeled antibody to the analyte; and the support is washed again. Analyte is detected by determining if the second antibody is bound to the support. In a competitive format, which can be either heterogeneous or homogeneous, a test sample is usually incubated with an antibody and a labeled competing antigen, either sequentially or simultaneously. These and other formats are well known in the art. Alternatively, a test sample may be a tissue section of a plant which is probed with an antibody to IG1 using methods well known to those in the art for detection of proteins in a tissue section with an antibody. Said tissue section may be from a plant being tested for natural expression of IG1 or a homolog or ortholog thereof. Alternatively, said tissue section may be from a plant which has been genetically altered by the means of the present invention or by some other means to express at least one protein selected from the group consisting of IG1, IG1-O, IG1-MUM, and homologs or orthologs thereof.

EXAMPLES

Example 1

Figure 3:
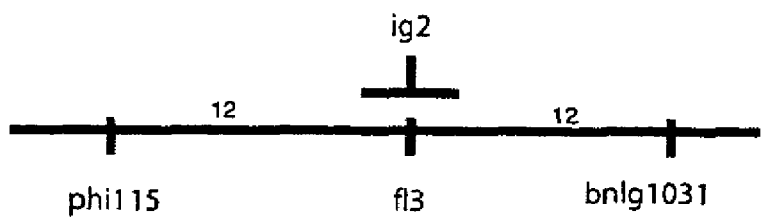
FIG. 3. Map position of ig2. Mapping with SSR's using the miniature seed phenotype as an indicator of the presence of the mutation placed ig2 midway between phi115 and bnlg1031. Mapping based on the reduced fertility phenotype using floury3 as a marker confirmed this position.

Characterize Newly Established Mutants with Extra Polar Nuclei ig2 has been mapped using Simple Sequence Repeat (SSR) markers and the floury3(fl3) mutation to chromosome 8 (FIG. 3). ig*-15791 does not show linkage to markers linked to ig1 or ig2 and consequently has been named ig3.

ig1, ig2, and ig3 have all been crossed to several inbred lines to determine their spectrum of phenotypic expression. ig1 shows good expression in W23, Mo17, W64A, and A158 but is suppressed in B73. ig2 shows good expression in B73, A158, and W64A but is suppressed in W23 and Mo 17. ig3 shows good expression in B73 and W23 and moderate expression in Mo 17 and is suppressed in W64A. From these results double mutants are being constructed of ig1 and ig2 in an A158 background. The frequency of miniature kernels produced by ig1, ig2 double mutants is the same as predicted if ig1 and ig2 interact additively.

Figure 4A:
FIG. 4. Mature ig2 seed phenotype. Mature seeds stained with Evans' Blue to detect cell death, ig2 (FIG. 4A); wild type (FIG. 4B). ig2 homozygotes undergo more extensive cell death in the endosperm than wild type, and it appears that it begins earlier. However, the embryos are still alive although abnormally shaped and smaller than wild type. They usually have a shoot pole with a few leaf primordia like wild type seeds.
Figure 4B:
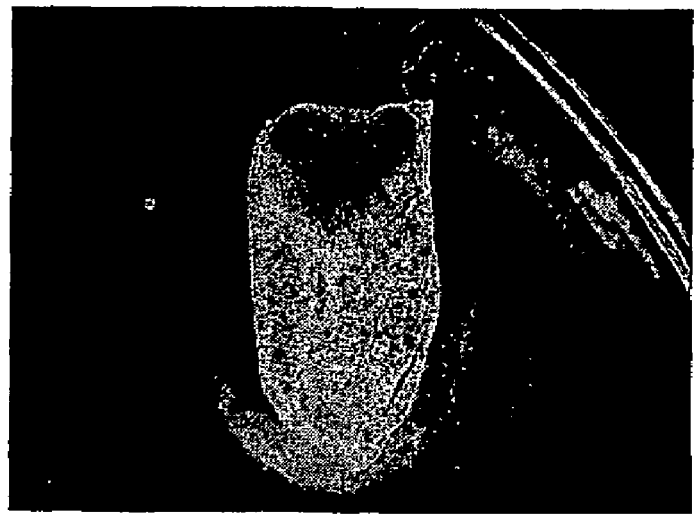
Figure 5:
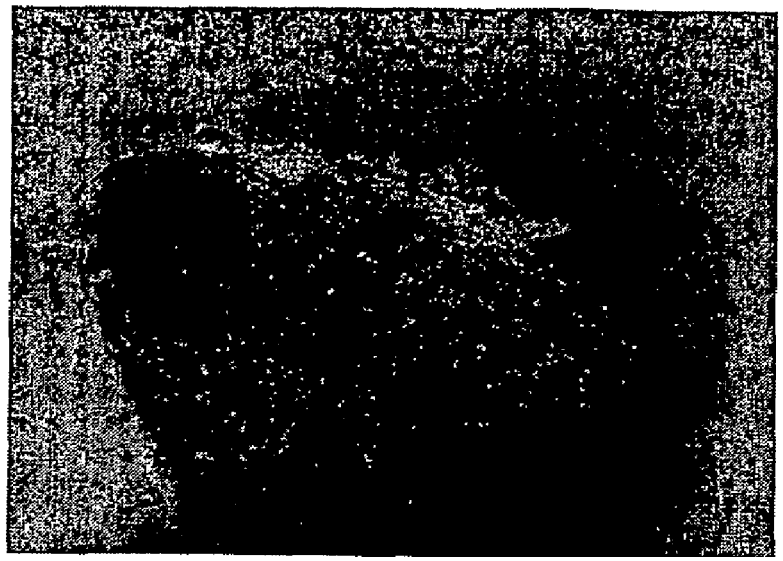
FIG. 5. Leaf of ig2 homozygote. The epidermis of the leaf has outgrowths and irregularly shaped cells. The seedling produced two abnormal leaves and then stopped growing.

Self-pollinations of ig2 and ig3 heterozygotes suggest mutant phenotypes of homozygous sporophytes. ig2 homozygotes are likely embryo lethal with an early aborting endosperm phenotype. In a W64A inbred background, the ig2 homozygous phenotype is slightly less severe. The endosperm undergoes extensive cell death and the embryo is small and abnormally shaped (FIG. 4). Some endosperm development occurs and seeds germinate to produce abnormal seedlings (FIG. 5). The epidermis of these plants is highly abnormal and irregular with swollen cells. ig3 homozygotes on the other hand are likely viable but have minor seed defects as seen by the increase in a variety of abnormal seed types in self-pollinations. Additionally, ig3 homozygotes may be male sterile in some backgrounds.

Figure 6:
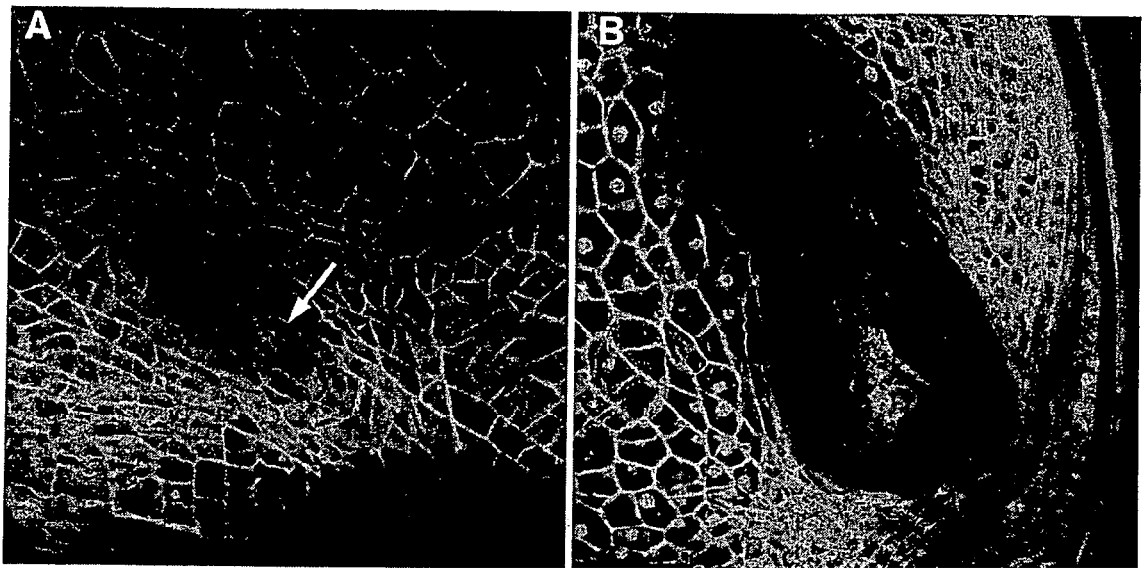
FIG. 6. Embryo sacs from an ig3 heterozygote.

To test for heterofertilization of ig2 and ig3 embryo sacs mutant heterozygotes in a B73 inbred background have been pollinated by B73 inbreds heterozygous at the r locus, carrying R-sc conferring aleurone and embryo color) and r-g (conferring a colorless aleurone and embryo). Control crosses onto standard B73 plants have also been made. The frequency of heterofertilization in crosses onto ig2 and ig3 heterozygotes is not significantly different from wild type. Early examination of ig3 embryo sacs has demonstrated that some of the mutant embryo sacs arrest early in megagametogenesis (FIG. 6).

Example 2

Cloning of Indeterminate Gametophyte1

Fine mapping of the ig1 gene was performed using the rice genome as a framework to order maize genes in the region of ig1. First an overall level of synteny was established between rice and maize around ig1 by taking the sequence of maize genetic markers and performing a Blast search against the rice genome sequence to find the most similar rice gene to each maize marker. This established rice chromosome 1 as the correct region to search for ig1. This analysis demonstrated that the majority of the maize markers fell in the same contig of rice chromosome 1 and the relative order of the markers was conserved.

Figure 7:
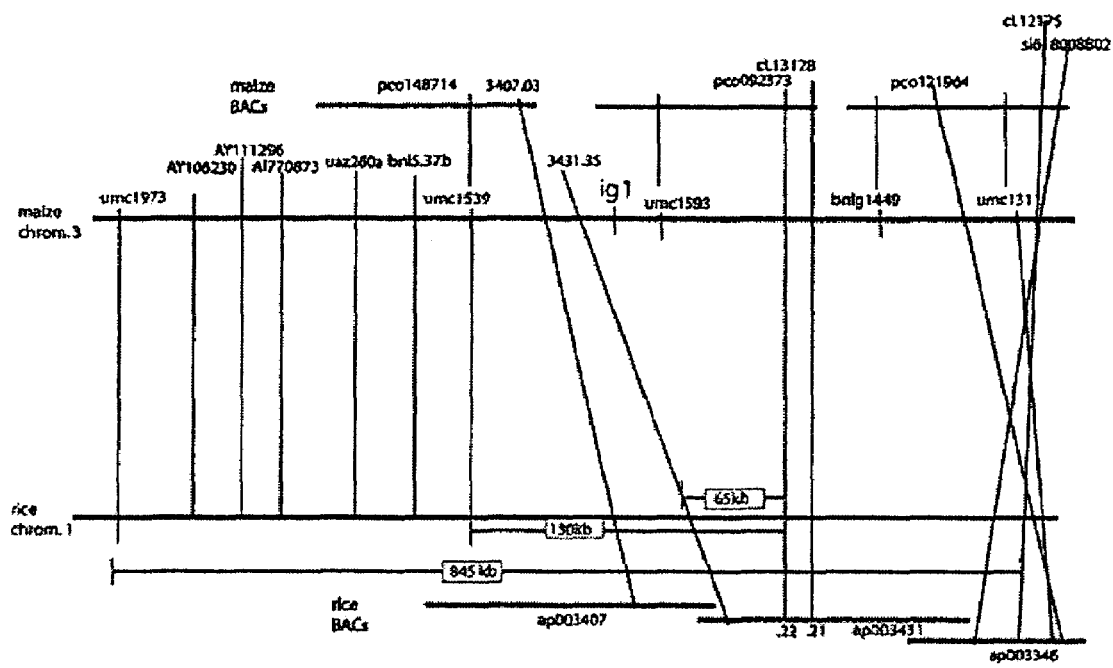
FIG. 7. Comparative mapping between rice and maize around ig1. Bacterial Artificial Chromosome (BAC) clones are shown by the three uppermost horizontal line segments (i.e., those labeled pco148714, pco092373, pco121964) and the three lowermost horizontal line segments (i.e., those labeled ap003407, ap003431, ap003346). Physical distance between markers on the rice chromosome is shown by the horizontal lines labeled "65 kb", "130 kb" and "845 kb". Vertical lines show the position of the closest sequence match in rice for maize clones from the ig1 region. Markers written above the maize BACs have been placed on the BAC clones but not on the genetic map.

Fine mapping of ig1 against these markers placed ig1 between umc1311 and umc1973 which have orthologs on rice chromosome 1 approximately 845 kilobases (kb) apart (FIG. 7). By generating mapping populations with multiple inbreds polymorphisms were found with other markers that further reduced this interval in the rice map to 378 kb on three rice Bacterial Artificial Chromosomes (BACs). At this point the available markers in the region in maize had been exhausted, so an attempt was made to use the rice genome sequence as displayed in the Gramene database to develop more maize markers.

Figure 8:
FIG. 8. Annotated genes between genes that should flank the rice ortholog of ig1 based on mapping of orthologous markers in maize.

Gene content of the region was inferred from the rice contig, and the sequences of the maize clones that matched these genes was used to design primers to develop PCR based mapping markers. Primers were first designed to amplify within exons, and amplicons were digested with several different restriction enzymes. These amplicons did not show any polymorphisms that could be used on the ig1 mapping population. However, by using the exon-intron structure of the rice genes as a guide for maize gene structure, primers were designed around maize introns and four out of eight were polymorphic. Two of these were useful in the mapping population. This reduced the interval in the rice genome predicted to contain the ig1 ortholog to 65 kb. The annotated genes in this interval are shown in FIG. 8.

Figure 9A:
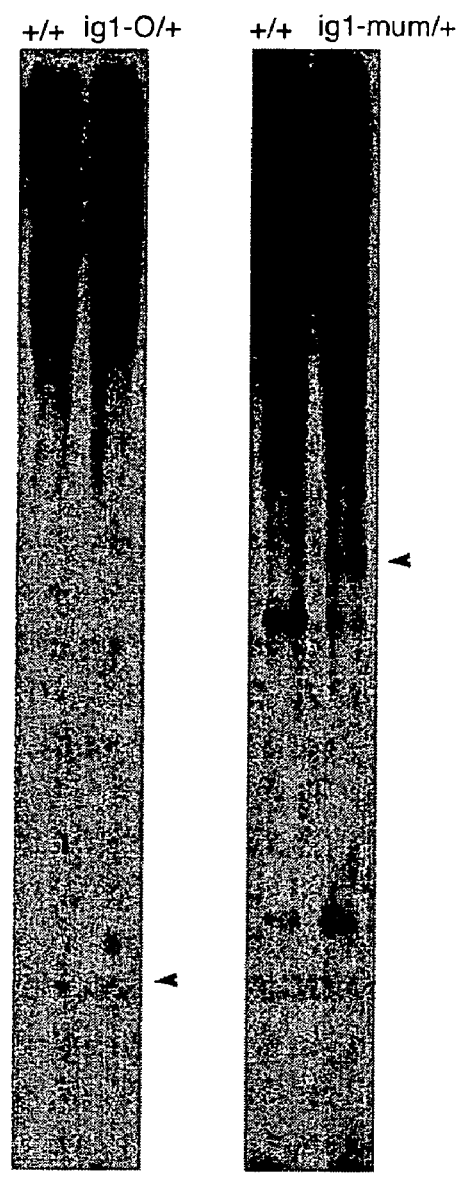
FIG. 9A. Polymorphisms in two independent ig1 alleles in the LOB domain gene. Southern blot of EcoR1 digested DNA probed with DNA flanking the Mu insertion in the LOB domain protein. (The probe used is probe 2-4 from FIG. 9B) Probe includes the LOB domain. DNA from mutant heterozygotes for ig1-O and ig1-mum is compared to that of their homozygous wild type progenitors. Arrowheads point to novel bands present in mutants that are absent from their wild type progenitors.

Non-complementation screens of 65,000 individuals produced seven male sterile selections as potential Mu alleles of ig1. After backcrossing, one of these new alleles has been proven to be heritable and to cause characteristic ig1 seed phenotypes. Mutant heterozygotes produce miniatures, aborted kernels, and twins. A cosegregating Mu element was found in a small population using a modified version of the Amplification of Insertion Mutagenized Sites protocol (AIMS) (Frey et al., 1998). This band was cloned and sequenced and found to be a Mu insertion in the LOB domain protein, the closest homolog of which lies in the rice genomic interval defined by the comparative mapping experiments. The DNA sequence flanking this insertion was used as a probe on a Southern blot with DNA from plants heterozygous for either the ig1-mum allele compared to its progenitor or the ig1-O allele compared to its progenitor. Both alleles have a novel band not found in their progenitors (i.e. both alleles have a new mutation in this gene) demonstrating that this is the ig1 gene (FIG. 9).

Figure 9B:
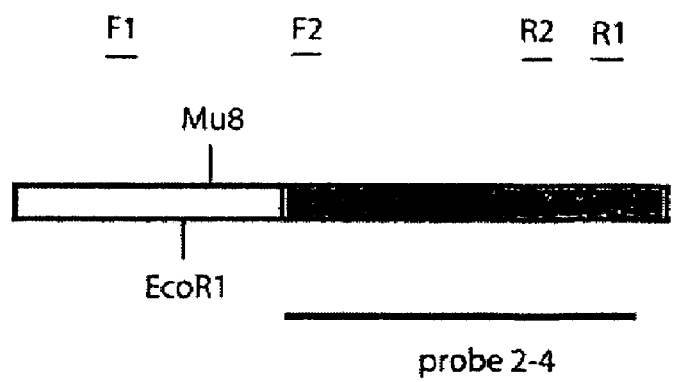
FIG. 9B. Structure of ig1 gene. Position of Mu insertion is noted and inferred to be a Mu8 element based on terminal inverted repeat sequence. Positions of primers used to amplify gene fragments are indicated. The LOB domain is indicated by the shading.

As additional evidence that the reference allele ig1-O carries a mutation in this same gene, PCR amplification of this gene was performed on homozygotes for ig1-O and its progenitor for several primer combinations (FIG. 9B). Primer R1 in combination with primer F1 or F2 generated a PCR product in wild type but failed to do so in ig1-O homozygotes. Primer R2 with either F1 or F2 generated a PCR product in wild type and mutant. These data suggest that the mutation in ig1-O lies between Primers R1 and R2 or within primer R1.

Thus, the ig1 gene was isolated using a combination of directed tagging and comparative mapping approaches. The partial nucleotide sequence of ig1 is provided in SEQ ID NO: 1 and the corresponding partial amino acid sequence of ig1 is provided in SEQ ID NO: 2. The ig1-O mutation is of unknown nature and occurs within base pair number 506 to base pair number 614 of SEQ ID NO: 1. The ig1-mum is a Mutator transposable element insertion between base pair number 173 and base pair number 174 of SEQ ID NO: 1.

Figure 2:
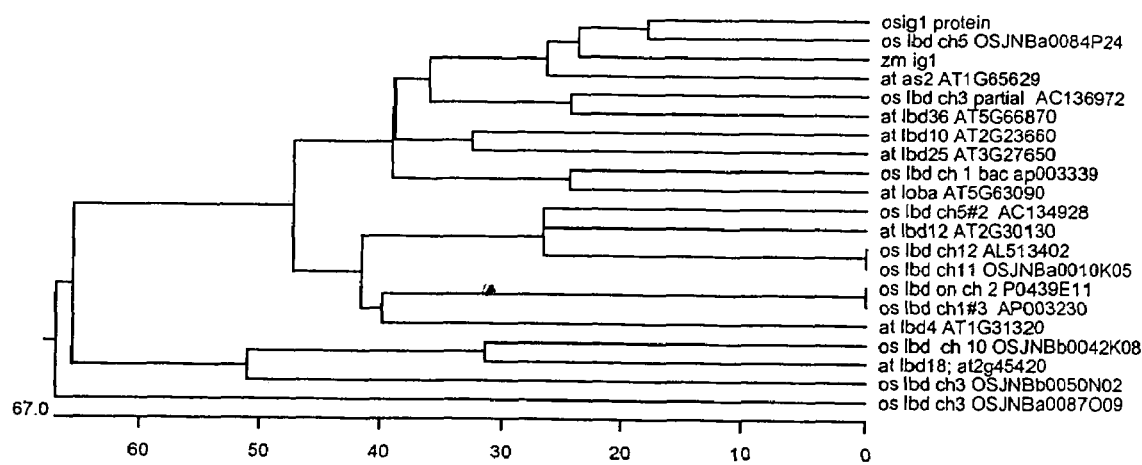
FIG. 2. IG1 protein and related proteins of rice and *Arabidopsis*. Rice proteins are designated as os lbd ch# (chromosome number) and BAC number. OSIG1 is the rice ortholog of IG1. *Arabidopsis* proteins are designated "at" followed by gene name and number. From the tree it can be seen that there are two rice genes that are closely related to ig1 and that ig1 and these two rice genes are most similar to AS2 in *Arabidposis*.

The ig1 gene encodes a member of the LATERAL ORGANS BOUNDARY (LOB) protein family (Shuai et al., 2002). This is a plant-specific gene family with 42 members in *Arabidopsis* (Shuai et al., 2002; Iwakawa et al., 2002). ig1 and its rice ortholog are most similar to ASYMMETRIC LEAVES2 in *Arabidopsis* (FIG. 2). The AS2 gene has been shown to repress the expression of the Knotted1-like homeobox (knox) genes KNA,T1/BREVIPEDICELLUS1 (BP1), KNAT2, and KNAT6 in leaf primordia (Ori et al., 2000; Semiarti et al., 2001; Xu et al., 2003; Lin et al., 2003). These genes are normally expressed in the shoot apical meristem but not in leaf primordia (Long et al., 1996; Lincoln et al., 1994). as2 loss-of-function mutations result in ectopic expression of knox genes in leaf primordia. This phenotype is also caused by loss-of-function mutations in the MYB-domain gene ASYMMETRIC LEAVES1 (Ori et al., 2000; Semiarti et al., 2001).

The maize ortholog of AS1, rough sheath2, has a similar role in repressing knox gene expression in leaf primordia demonstrating conservation of function in dicots and monocots (Schneeberger et al., 1998; Timmermans et al., 1999; Tsiantis et al., 1999). AS2 is a nuclear protein that interacts physically with AS1 protein, suggesting a role for LOB domain genes in regulating transcription (in the case of AS2 in combination with AS1) (Iwakawa et al., 2002; Xu et al., 2003). It is not yet known whether AS1 and AS2 repress transcription of knox genes directly or indirectly. Interestingly, regarding the role of ig1 in restricting the embryogenic potential of cells lacking a maternal or paternal genome, as2 mutants have an enhanced ability to develop autonomous shoots in vitro (Semiarti et al., 2001). To date no effect of as2 on the female gametophyte has been reported. The molecular identity of ig1 suggests that common mechanisms have been used in regulating the number of nuclear-cytoplasmic domains in the embryo sac and stem cell identity in the shoot.

Example 3

Screening for Additional Mutants with Extra Polar Nuclei

Two new isolates were identified that produced plump endosperms and triploid embryos when pollinated with pollen from a tetraploid plant. One of these was recovered by outcrossing as a pollen parent followed by retesting as a female and shown to have ig1-like seed phenotypes. This verified polar nuclei number mutant arose in a Mutator transposable element line.

Example 4

Expression Pattern of ig1

Developing tassels and ears of wild-type plants are fixed and sectioned according to the protocol of Jackson et al. (1991). The 3' portion of the ig1 gene is to be used for a probe for in situ hybridization because the amino terminus of the protein carries the conserved LOB domain while the carboxy terminus is divergent among members of the LOB gene family. Specifically, the time of expression of ig1 during megagametogenesis is established.

Example 5

Test for a Role for as2 or One of the Closely Related Genes in the *Arabidopsis* Embryo Sac AS2 falls into a clade of LOB genes with 4 other members that are more closely related than the others (FIG. 2 and Iwakawa et al., 2002). These are LBD36/ASL1, LBD10/ASL2, LBD25/ASL3, and LOBa/ASL4.

Testing for expression of the most closely related LOB genes in the embryo. Knowing which of these genes is expressed in the embryo sac is useful in determining which may be carrying out ig1 function in *Arabidopsis thaliana*. Microarray data has been analyzed on the expression of some of these genes in flowers and other tissues and they have been compared to the expression of genes known to be required in the embryo sac: DEMETER (DME), MEDEA (MEA), and FERTILIZATION INDEPENDENT ENDOSPERM (FIE) (Table 1). None of these genes is expressed at high levels in any tissue tested. Unfortunately, the small number of cells contributed to the flower by the embryo sac makes it difficult or impossible to distinguish embryo sac gene expression in this manner, as evidenced by the extremely low values for MEA in the flower despite the fact that it is required in the embryo sac. Consequently, expression of AS2 and its four closest relatives are examined in the embryo sac using in situ hybridization. Probes from the 3' end of the cDNAs for these genes are used to prevent cross hybridization. These experiments are used to determine which of these family members are expressed in the embryo sac. This information helps establish which one(s) carry out the role of the ig1 gene in the embryo sac of *Arabidopsis*.

TABLE 1

Microarray analysis of expression levels of some LOB domain genes and gametophyte required genes in *Arabidopsis*

|  | AS2 | LBD10 | LBD25 | DME | MEA | FIE |
|---|---|---|---|---|---|---|
| flower average | 309 | 337 | 42 | 147 | 16 | 235 |
| leaf average | 191 | 524 | 50 | 244 | 171 | 283 |
| root average | 84 | 175 | 93 | 133 | 12 | 254 |
| seedling average | 100 | 215 | 183 | 124 | 11 | 184 |
| silique average | 238 | 193 | 20 | 60 | 14 | 293 |
| stem average | 27 | 307 | 52 | 119 | 34 | 166 |

Examination of mutant phenotypes of knockouts of the genes that are expressed in the embryo sac. If expression pattern does not distinguish them, they are examined in order of similarity to ig1. Since ig1 bears the most similarity to AS2, as2 are examined first for embryo sac defects using Confocal Laser Scanning Microscopy according to the method of Christensen et al. (1997). Specifically, embryo sacs are examined for the presence of extra rounds of free nuclear divisions and improper placement of nuclei during the syncytial phase of development. If no defects are detected in as2, knockouts in the five most closely related genes are examined in a similar fashion next; these genes are LBD36/ASL1, LBD1O/ASL2, LBD25/ASL3, and LOBa/ASL4. T-DNA insertions are available for all of these genes except LBD36/ASL1 for which there are two EMS induced TILLING alleles in conserved amino acid residues. It is possible that there is genetic redundancy present in *Arabidopsis* that is not present in maize (and vice versa). If none of the single mutants display an ig-like phenotype, then double mutants are tested starting with as2 and its closest relative lbd36/as11 followed by as2 lbd10/as12 doubles, lbd36 lbd10, and /bd25 loba. If these all have a wild type embryo sac phenotype, the triple mutant between as2, lbd36/as11, and lbd10/as12 will be constructed and tested next because these three are grouped together more closely than LBD25/ASL3 and LOBa/ASL4.

Example 6

Test for a Role of Knox Genes in the ig1 Phenotype

Test for ectopic expression of knox genes in ig1 mutant embryo sacs. Because ig1 is most similar to AS2 in *Arabidopsis* it raises the possibility that the mutant phenotype is caused by a similar mechanism, i.e., misexpression of knox genes, but in this case in the embryo sac rather than in leaves. The lack of a leaf phenotype in ig1 mutants may reflect genetic redundancy in maize not present in *Arabidopsis*. However, it is not yet known if either mutant allele is a complete loss of function.

Expression of rs1, kn1, lg3, lg4, and gn1 in ig1 mutant and wild type ovules is examined by in situ hybridization to determine if any of these genes are ectopically expressed in mutant embryo sacs.

Phenocopying the ig1 mutant by misexpressing knox genes. The as2 and rs2 leaf phenotypes are mimicked by ectopically expressing knox genes in leaf primordia in both *Arabidopsis* and maize (Chuck et al., 1996; Schneeberger et al., 1995). To test if ig1 are mimicked by similarly expressing knox genes in the embryo sac, knat1/bp1 and stm are expressed using promoters that can drive expression specifically in the embryo sac. Three different promoters are to be tested, those of DEMETER (DME), MEDEA (MEA), and FERTILIZATION INDEPENDENT SEED2 (FIS2). The promoter sequences to be used are: for DME the 2282 base pairs 5' of the start site; for MEA the 2,070 base pairs upstream of the translational start site; and for FIS2 the 3,189 base pairs upstream of the translational start site. These promoters have been shown to drive expression of B-glucuronidase and Green fluorescent protein in embryo sacs without expression in other parts of the ovule, although MEA and FIS2 show expression after fertilization (Luo et al., 2000; Choi et al., 2002).

However, expression from these promoters in other parts of the plant has not been reported. If these constructs cause defects in the sporophyte that make it difficult to score the embryo sac phenotype, a different strategy will be taken. The DME promoter is used to drive expression of a protein fusion of BP1/KNAT1 and the steroid binding domain of the glucocorticoid receptor. A similar protein fusion has been used to ectopically express KNOTTED1 in leaves with the CaMV35S promoter (Hay et al., 2003). Dexamethasone is added to floral buds to activate the protein fusion in the embryo sac cells expressing it. Ovules are then be cleared and examined for extra rounds of free nuclear divisions. This should prevent expression of bp1/knat1 in tissues outside of the flower.

Test if kn1 loss-of-function suppresses the ig1 phenotype. If misexpression of kn1 causes the ig1 embryo sac phenotype, then kn1 loss of function should suppress the ig1 phenotype. Double mutants between ig1 and kn1 are constructed to test this. kn1 homozygotes have meristem defects that interfere with floral production. However, since the action of ig1 is during the haploid generation, the plants to be tested are ig1/+kn1/+ double heterozygotes which will produce the critical ig1 kn1 double mutant embryo sacs. Seeds with ig1 phenotypes (i.e. miniatures and twins) are tested for the presence of the kn1 mutation. If kn1 suppresses ig1, then these seeds should be less likely to carry the mutant allele than normal seeds.

If knockouts of any of the LOB domain genes have an ig1 phenotype in *Arabidopsis*, double (or triple) mutants are constructed between bp1 and the appropriate lob mutant(s). The frequency of extra rounds of free nuclear divisions in the embryo sac are compared between bp1 lob double mutants and lob single mutants. If the ig1-like phenotype is a consequence of ectopic expression of bp1, then this phenotype should be suppressed by the bp1 mutation.

Example 7

Test for Interactions Between ig1 and rs2

Use of yeast 2 hybrids to look for physical interaction between IG1 and RS2 protein. To further test if ig1 is the ortholog of AS2 the IG1 protein is tested for the ability to interact with RS2 protein (the AS1 ortholog). This is performed in yeast two-hybrid assays similarly to that done for AS1 and AS2 (Xu et al., 2003). Briefly, IG1 and RS2 is tested as both bait and prey in the MATCHMAKER two-hybrid vectors pGADT7 and pGBKT7 (Clonetech, USA). Interaction is indicated by the ability of yeast to grow on media lacking tryptophan, leucine, histidine, and adenine only in the presence of both proteins but not in the presence of only one or neither of them.

Examination of ig1; rs2 double mutants for both embryo sac and leaf phenotypes. A genetic test for interaction between ig1 and rs2 is performed by constructing double mutants. Although rs2 has no reported embryo sac phenotype and ig1 has no leaf phenotype, these mutations may enhance one another. Plants heterozygous for ig1 and heterozygous for rs2 are scored for severity of ig1 embryo sac phenotypes (i. e. frequency of miniatures, twins, and transmission of ig1 and rs2) to test if rs2 can enhance ig1 phenotypes. Double homozygotes for rs2 and ig1 are examined for the severity of rs2 leaf phenotypes to test if ig1 can enhance rs2 phenotypes.

Example 8

Knock out the Rice ig1 Ortholog and Test for an Increase in Maternal and Paternal Haploid Production Because of the agronomic utility of the ig1 mutant in maize breeding the ability to apply this to other species could be beneficial to their breeding programs. This is tested in rice by knocking out the rice ig1 ortholog, *Oryza sativa* ig1 (osig1). A T-DNA insertion has been identified in osig1 in the 5' region of the gene in the Plant Functional Genomics Lab. Dept. of Life Science, POSTECH in Kyoungbuk, Korea. This line is tested for reduction in the mRNA levels of the gene. If osig1 RNA levels are reduced in the mutant, then it is be examined for ig1 like phenotypes. These plants are tested for paternal haploid production by pollinating with a different rice strain and testing the progeny by PCR for loss of maternal alleles of polymorphic Simple Sequence Repeat loci in seedlings. As plants homozygous for paternal alleles cannot be generated by self-pollination, rare self-pollination contaminants will not interfere with their identification.

If the T-DNA insertion does not reduce osig1 RNA levels, transgenic rice plants are to be generated carrying a-construct that can reduce osig1 expression levels. The 3' end of osig1 is to be cloned into an RNA interference (RNAi) vector in both orientations around a central linker and transformed into rice plants. This will cause expression of the mRNA as a double stranded RNA leading to degradation of osig1 mRNA by post-transcriptional gene silencing. RNAi has been shown to work in rice as a tool to reduce expression of the rice APETALA3 ortholog (Xiao et al., 2003). By using the less conserved 3' end any affect on other lob genes in rice should be prevented. However, because of the possibility of redundancy of ig function in rice that may or may not be present in maize (see FIG. 2), the sequence to clone into the RNAi vector is chosen to match osig1 and its closest partner, the os lbd gene on chromosome 5 BAC OSJNBa0084P24. As a first test, this interfering RNA is expressed under control of the native osig1 promoter using four kilobases of sequence upstream of the translation start site; this includes all of the sequence upstream of osig1 up to the next annotated gene. If this causes severe sporophyte phenotypes that interfere with seed production, then the native osig1 promoter is used to drive expression of the glucocorticoid receptor. A glucocorticoid responsive promoter similar to that of Aoyama and Chua (1997) is then be used to drive expression of the interfering RNA, the expression of which can be induced in flowers using dexamethasone.

Example 9

Disabling or Eliminating Expression of ig1

The isolated ig1 gene and vectors comprising the gene as provided by the present invention can be used to disable or eliminate ig1 gene function in the tassel to obtain male sterility in maize and in other plant species. For example, using the knock-out/knock-in technology described previously, the normal or wild type ig1 gene can be replaced with a construct comprising an ig1 gene operably linked to a tassel-specific promoter that activates a gene that causes the ig1 gene not to be expressed or results in the loss of function of the ig1 gene in the pollen and/or tassel. Examples of pollen-specific and tassel-specific promoters were discussed previously. Thus, when the introduced construct is expressed in the tassel, the ig1 gene is disabled or eliminated, thereby leading to the production of sterile pollen. Using this procedure would not result in the disablement or elimination of the ig1 gene in the cells that are not located in the tassel.

Alternatively, the tassel-specific promoter could be linked to another gene that inactivates the ig1 gene in the tassel only when a certain compound is present. For example, the gene that inactivates the ig1 gene may only be expressed when the tassels are sprayed with a specific compound.

Example 10

Rescuing the ig1 Mutant Phenotype in the Tassel

Rescuing an ig1 mutant phenotype in all tissues except in the tassel can also produce male sterile maize and male sterility in other plant species. For example, utilizing the nucleic acid sequence of the ig1 gene as provided by the present invention, a mutation could be introduced into the ig1 gene using knock-in technology or via site-directed mutation, or a mutant ig1 gene could replace the normal or wild type ig1 gene by using knock-out/knock-in technology. In this system, a construct could either be introduced with the knock-in technology or separately wherein the construct includes a genetic system that will rescue the ig1 mutant so that it functions in all of the cells except those in the tassel.

Example 11

Downregulation of ig1 Orthologs

As discussed previously, the isolated ig1 maize gene of the present invention can be used as a probe to locate orthologs of the ig1 gene in other plant species. Then, down-regulation of the ig1 ortholog(s) in plants other than maize (e.g., rice, wheat, sorghum, soybean) will effectively generate ig1 mutants in these species leading to the production of androgenic haploid and diploid plants. This down-regulation can be achieved either by identifying mutations in the gene(s) or by using transgenic technology. Transgenic methods of down-regulation were discussed previously, including but not limited to anti-sense technology and co-suppression.

Example 12

Ectopically Expressing Genes Repressed by Expression of ig1

Ectopically expressing genes (e.g., knotted-like homeobox genes) that would normally be repressed by the ig1 gene in the female gametophyte of maize or other plants can be used to mimic loss-of-function mutant phenotypes for the purpose of generating androgenic haploid and diploid progeny (i.e., progeny that lack a maternal contribution to their genome).

Example 13

Ectopic Expression of ig1

Ectopic expression of the ig1 gene can also be used to create plant cultivars that produce embryos that are clones of the parent plant by apomixis.

It must be noted that as used in this specification and the appended claims, the singular forms "a," "and," and "the" include plural referents unless the contexts clearly dictates otherwise. Thus, for example, reference to "a metal" includes mixtures and large numbers of such metals and heavy metals, reference to "a transgenic plant" includes large numbers of transgenic plants and mixtures thereof, and reference to "the method" includes one or more methods or steps of the type described herein.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited.

REFERENCES

ALBERTSEN, M. C. AND TRIMNELL, M. R. (1990) Agronomic comparisons among ig-derived and backcross-derived CMS maize lines. Agron. Abst. Am. Soc. Agron., Madison, Wis., p. 78.

AOYAMA, T AND CHUA, N-H. (1997) A glucocorticoid-mediated transcriptional induction system in transgenic plants. Plant J. 11: p.605-612.

CHOI, Y, GEHRING, M, JOHNSON, L, HANNON, M, HARADA, J J, GOLDBERG, R B, JACOBSEN, S E, AND R L FISCHER. (2002) DEMETER, a DNA glycosylase domain protein, is required for endosperm gene imprinting and seed viability in Arabisopsis. Cell 110: 33-42.

CHRISTENSEN, C. A., GORSICH, S W, BROWN, R H, JONES, L G, BROWN, J, SHAW, J M, AND DREWS, G. N. (2002) Mitochondrial GFA2 is required for synergid cell death in Arabidopsis. Plant Cell 14: 2215-2232.

CHRISTENSEN, C. A., KING, E. J., JORDAN, J. R., AND DREWS, G. N. (1997) Meagametogenesis in Arabidopsis wild type and the Gf mutant. Sex. Plant Reprod. 10: 49-64.

CHRISTENSEN, C. A., SUBRAMANIAN, S., AND DREWS, G. N. (1998) Identification of gametophytic mutations affecting female gametophyte development in Arabidopsis. Dev. Biol. 202: 136-151.

CHUCK, G, LINCOLN, C, AND S HAKE. (1996) KNAT1 induces lobed leaves with ectopic meristems when overexpressed in Arabidopsis. Plant Cell 8: 1277-1289.

COE, E. H., NEUFFER, M. G. & HOISINGTON, D. A. (1988) The genetics of corn. Pp. 81-258. In Corn and Corn Improvement, G. F. Sprague and J. W. Dudley, eds. Amer. Soc. Agronomy, Inc., Madison Wis.

DREWS, G. N., LEE, D., and C. A. CHRISTENSEN, (1998) Genetic Analysis of Female Gametophyte Development and Function. Plant Cell 10: 5-18.

FELDMANN, K. A., COURY, D. A., AND CHRISTIANSON, M. L. (1997) Exceptional segregation of a selectable marker ($Kan^R$) in Arabidopsis identifies genes important for gametophyte growth and development. Genetics 147: 1411-1422.

FREY, M., STETTNER, C., AND GIERL, A. (1998) A general method for gene isolation in tagging approaches: amplification of insertion mutagenised sites (AIMS). Plant J. 13: 717-721.

GROSSNIKLAUS, U., and K. SCHNEITZ, (1998) The molecular and genetic basis of ovule and megagametophyte development. Sem. Cell Devl. Biol. 9: 227-238.

HAY, A; JACKSON, D; ORI, N; AND S HAKE. (2003) Analysis of the competence to respond to KNOTTED 1 activity in Arabidopsis leaves using a steroid induction system. Plant Physiology 131: 1671-1680.

HOWDEN, R., PARK, S. K., MOORE, J. M., ORME, J., GROSSNIKLAUS, U., AND TWELL, D. (1998) Selection of T-DNA-Tagged male and female gametophytic mutants by segregation distortion in Arabidopsis. Genetics 149: 621-631.

HUANG, B.-Q. AND SHERIDAN, W. F. (1996) Embryo sac development in the maize indeterminate gametophyte1 mutant: abnormal nuclear behavior and defective microtubule organization. Plant Cell 8: 1391-1407.

IWAKAWA, H, UENO, Y, SEMIARTI, E, ONOUCHI, H, KOJIMA, S ET AL. (2002) The ASYMMETRIC LEAVES2 gene of Arabidopsis thaliana, required for formation of a symmetric flat lamina, encodes a member of a novel family of proteins characterized by cysteine repeats and a leucine zipper. Plant Cell Physiol. 43: 467-478.

JACKSON, D. (1991) In situ hybridization in plants. In Molecular Plant Pathology: A Practical Approach, (ed. D J Bowles, S J Gurr and M McPherson), pp. 163-174. Oxford: Oxford University Press.

KERMICLE, J. L. (1969) Androgenesis conditioned by a mutation in maize. Science 166: 1422-1424.

KERMICLE, J. L. (1971) Pleiotropic effects on seed development of the indeterminate gametophyte gene in maize. Amer. J. Bot. 58: 1-7.

KERMICLE, J. L. (1994) Indeterminate gametophyte (ig): biology and use. In The Maize Handbook. New York: Springer-Verlag. 388-393.

KINDIGER. B. AND HAMANN, S. (1993) Generation of haploids in maize: a modification of the indeterminate gametophyte (ig) system. Crop Sci. 33: 342-344.

LIN, B.-Y. (1978) Structural modifications of the female gametophyte associated with the indeterminate gametophyte (ig) mutant in maize. Can. J. Genet. Cytol. 20: 249-257.

LIN, B.-Y. (1981) Megagametogenetic alterations associated with the indeterminate gametophyte (ig) mutation in maize. Rev. Bras. Biol. 41: 557-563.

LIN, W-C, SHUAI, B, AND PS SPRINGER (2003) The Arabidopsis LATERAL ORGAN BOUNDARIES-Domain Gene ASYMMETRIC LEAVES2 Functions in the Repression of KNOX Gene Expression and in Adaxial-Abaxial Patterning. Plant Cell 15: 2241-2252

LINCOLN C, LONG J, YAMAGUCHI J, SERIKAWA K, HAKE S. (1994). A Knotted1-like homeobox gene in *Arabidopsis* is expressed in the vegetative meristem and dramatically alters leaf morphology when overexpressed in transgenic plants. Plant Cell 6:1869-76

LONG J A, MOAN E I, MEDFORD J I, BARTON M K. (1996). A member of the KNOTTED class of homeodomain proteins encoded by the STM gene of *Arabidopsis*. Nature 379:66-69

LUO, M., BILODEAU, P., DENNIS, E. S., PEACOCK, W. J., & CHAUDHURY, A . (2000). Expression and parent-of-origin effects for FIS2, MEA, and FIE in the endosperm and embryo of developing *Arabidopsis* seeds. Proc. Natl. Acad. Sci. USA 97, 10637-10642.

MOORE, J. M., VIELLE CALZADA, J.-P., GAGLIANO, W., AND GROSSNIKLAUS, U. (1997) Genetic characterization of hadad, a mutant disrupting female gametogenesis in *Arabidopsis thaliana*. Cold Spring Harbor Symp. Quant. Biol. 42: 35-47.

ORI, N, ESHED, Y, CHUCK, G, BOWMAN, J L, AND S HAKE. (2000) Mechanisms that control knox gene expression in the *Arabidopsis* shoot. Development 127: 5523-5532.

PATTERSON, E. B. 1978. Properties and uses of duplicate-deficient chromosome complements in maize. pp. 693-710. In Maize breeding and genetics, D. B. Walden ed. John Wiley and Sons, New York.

SCHNEEBERGER, R G, BECRAFT, P W, HAKE, S, AND M FREELING (1995). Ectopic expression of the knox homeobox gene rough sheath 1 alters cell fate in the maize leaf. Genes Dev. 9: 2292-2304.

SCHNEEBERGER, R., TSIANTIS, M., FREELING, M., AND LANGDALE, J. A. (1998). The rough sheath2 gene negatively regulates homeobox gene expression during maize leaf development. Development 125, 2857-2865.

SEMIARTI, E, UENO, Y, TSUKAYA, H, IWAKAWA, H, MACHIDA, C, AND Y MACHIDA (2001) The ASYMMETRIC LEAVES2 gene of *Arabidopsis thaliana* regulates formation of a symmetric lamina, establishment of venation and repression of meristem-related homeobox genes in leaves. Development 128: 1771-1783.

SHIMIZU, K K AND OKADA, K (2000) Attractive and repulsive interactions between female and male gametophytes in *Arabidopsis* pollen tube guidance. Development 127: 4511-4518.

SHUAI, B, REYNAGA-PENA, C G, AND P S SPRINGER. (2002) The LATERAL ORGAN BOUNDARIES gene defines a novel, plant-specific gene family. Plant Physiol. 129: 747-761.

SPRINGER, P. S., MCCOMBIE, W. R., SUNDARESAN, V., AND MARTIENSSEN, R. A. (1995) Gene trap tagging of PROLIFERA, an essential MCM2-3-5-like gene in *Arabidopsis*. Science 268: 877-880.

TIMMERMANS, M. C. P., HUDSON, A., BECRAFT, P. W., AND NELSON, T. (1999). ROUGH SHEATH2: A Myb protein that represses knox homeobox genes in maize lateral organ primordia. Science 284, 151-153.

TSIANTIS, M., SCHNEEBERGER, R., GOLZ, J. F., FREELING, M., AND LANGDALE, J. A. (1999). The maize rough sheath2 gene and leaf development programs in monocot and dicot plants. Science 284, 154-156.

WALBOT, V. and EVANS, M. M. S. (2003) Unique features of the plant life cycle and their consequences. Nature Rev. Genet., 4: 369-379.

XU, L, XU, Y, DONG, A, SUN, Y, PI, L, XU, Y, AND H HUANG. (2003) Novel as1 and as2 defects in leaf adaxial-abaxial polarity reveal the requirement for ASYMMETRIC LEAVES1 and 2 and ERECTA functions in specifying leaf adaxial identity. Development 130: 4096-4107.

YANG, W.-C. and V. SUNDARESAN, 2000 Genetics of gametophyte biogenesis in *Arabidopsis*, Curr. Opinion Plant Sci. 3: 53-57.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An isolated nucleic acid molecule having at least 99% identity to SEQ ID NO: 1.

2. An isolated nucleic acid molecule comprising SEQ ID NO: 1.

3. The isolated nucleic acid molecule of claim 1, wherein the nucleic acid molecule is operably linked to one or more expression control elements.

4. A vector comprising the isolated nucleic acid molecule of claim 1, wherein the isolated nucleic acid molecule is operably linked to a promoter.

5. A maize plant cell transformed to contain the nucleic acid molecule of claim 1, wherein the nucleic acid molecule is operably linked to a promoter.

6. A maize plant cell comprising the vector of claim 4.

7. A transgenic maize plant which comprises at least one copy of the nucleic acid molecule of claim 1, wherein the nucleic acid molecule is operably linked to a promoter.

8. A transgenic maize plant which comprises at least one copy of the nucleic acid molecule of claim 3.

9. The vector of claim 4, for the down-regulation of IG1, wherein the nucleic acid molecule is operably linked to a promoter in an antisense orientation.

10. A method for down regulating ig1 RNA levels in a plant, the method comprising the step of introducing the vector of claim 9 into a plant tissue, wherein transcription of RNA from the nucleic acid molecule causes down-regulation of expression of ig1 RNA in the plant tissue, wherein the plant is a maize.

11. The method of claim 10, wherein the RNA is double-stranded.

12. The method of claim 10, wherein the RNA is an antisense RNA.

13. An RNA molecule that down regulates expression of an ig1 gene, wherein the RNA molecule comprises a nucleotide sequence that is complementary to the entire nucleic acid molecule of claim 1.

14. The RNA molecule of claim 13, wherein the RNA molecule is double-stranded.

* * * * *

SEQUENCE LISTING

```
<160> NUMBER OF SEQ ID NOS: 2

<210> SEQ ID NO 1
<211> LENGTH: 649
<212> TYPE: DNA
<213> ORGANISM: Zea mays
<220> FEATURE:
<221> NAME/KEY: misc_feature
<222> LOCATION: (173)..(174)
<223> OTHER INFORMATION: transposon insertion site
<220> FEATURE:
<221> NAME/KEY: CDS
<222> LOCATION: (261)..(647)
<220> FEATURE:
<221> NAME/KEY: misc_feature
<222> LOCATION: (506)..(614)
<223> OTHER INFORMATION: region where ig1-0 mutation occurs

<400> SEQUENCE: 1
```

```
accagcaggt aggtcttcct cacctcgctg ctgtgcgaaa gcgagcacac aacaaaccct     60
aacttactat ttgtattcgg atctgatcta ctggatccgc cctgatttg aggcagtatt     120 cctcatattt ggcaaaggag gccgaattcc agccagattc tctattctcc ccctgatttc    180
cagcagcttc caaaactttc taagaaaca aagaagagt ctaacacagc tcgtgatcct      240
tccgccaggg cagcagacgg atg gct tcg tcg gtg ccg gcg cca tcg ggg tcg   293
                       Met Ala Ser Ser Val Pro Ala Pro Ser Gly Ser
                        1               5                  10 gtg atc acc gtg gcg tcg tct tct tcc tca gca gcc gcg gcc gcg gtg     341
Val Ile Thr Val Ala Ser Ser Ser Ser Ser Ala Ala Ala Ala Ala Val
            15                  20                  25 tgc ggc acg ggc tcc cca tgc gct gcg tgc aag ttc ctg cgt cgc aag     389
Cys Gly Thr Gly Ser Pro Cys Ala Ala Cys Lys Phe Leu Arg Arg Lys
        30                  35                  40 tgc cag ccg gac tgc gtg ttc gcg ccc tac ttc cca ccg gac aac ccg     437
Cys Gln Pro Asp Cys Val Phe Ala Pro Tyr Phe Pro Pro Asp Asn Pro
    45                  50                  55 cag aag ttc gtg cac gtg cac cgc gtc ttc ggc gcg agc aac gtg acc     485
Gln Lys Phe Val His Val His Arg Val Phe Gly Ala Ser Asn Val Thr
60                  65                  70                  75 aag ctg ctg aac gag ctc cac ccc ttc cag cgc gag gac gcc gcg aac     533
Lys Leu Leu Asn Glu Leu His Pro Phe Gln Arg Glu Asp Ala Ala Asn
                80                  85                  90 tcc ctc gcc tac gag gcc gac atg cgc ctc cgc gac ccc gtc tac ggc     581
Ser Leu Ala Tyr Glu Ala Asp Met Arg Leu Arg Asp Pro Val Tyr Gly
            95                 100                 105 tgc gtc ggc gtc atc tcc atc ctc cag cac aac cta cga cag ctc cag    629
Cys Val Gly Val Ile Ser Ile Leu Gln His Asn Leu Arg Gln Leu Gln
        110                 115                 120 cag gac ctc ccc ccg cgc ca                                          649
Gln Asp Leu Pro Pro Arg
    125

<210> SEQ ID NO 2
<211> LENGTH: 129
<212> TYPE: PRT
<213> ORGANISM: Zea mays

<400> SEQUENCE: 2

Met Ala Ser Ser Val Pro Ala Pro Ser Gly Ser Val Ile Thr Val Ala
 1               5                  10                  15

Ser Ser Ser Ser Ser Ala Ala Ala Ala Val Cys Gly Thr Gly Ser
            20                  25                  30

Pro Cys Ala Ala Cys Lys Phe Leu Arg Arg Lys Cys Gln Pro Asp Cys
        35                  40                  45

Val Phe Ala Pro Tyr Phe Pro Pro Asp Asn Pro Gln Lys Phe Val His
    50                  55                  60

Val His Arg Val Phe Gly Ala Ser Asn Val Thr Lys Leu Leu Asn Glu
65                  70                  75                  80

Leu His Pro Phe Gln Arg Glu Asp Ala Ala Asn Ser Leu Ala Tyr Glu
                85                  90                  95

Ala Asp Met Arg Leu Arg Asp Pro Val Tyr Gly Cys Val Gly Val Ile
            100                 105                 110

Ser Ile Leu Gln His Asn Leu Arg Gln Leu Gln Gln Asp Leu Pro Pro
        115                 120                 125

Arg
```